US00RE47607E

(19) United States
(12) Reissued Patent
Leu et al.

(10) Patent Number: US RE47,607 E
(45) **Date of Reissued Patent: *Sep. 17, 2019**

(54) LUCIFERASE SIGNAL ENHANCING COMPOSITIONS

(71) Applicant: GENE STREAM PTY LTD, City Beach (AU)

(72) Inventors: Marco Peter Leu, Aesch (CH); John Michael Daly, Perth (AU)

(73) Assignee: GENE STREAM PTY LTD., City Beach (AU)

( * ) Notice: This patent is subject to a terminal disclaimer.

(21) Appl. No.: 15/292,259

(22) Filed: Oct. 13, 2016

Related U.S. Patent Documents

Reissue of:
(64) Patent No.: 8,232,047
Issued: Jul. 31, 2012
Appl. No.: 12/446,777
PCT Filed: Oct. 24, 2007
PCT No.: PCT/AU2007/001615
§ 371 (c)(1),
(2) Date: Nov. 2, 2009
PCT Pub. No.: WO2008/049160
PCT Pub. Date: May 2, 2008

U.S. Applications:
(62) Division of application No. 14/447,935, filed on Jul. 31, 2014, now Pat. No. Re. 46,199, which is an application for the reissue of Pat. No. 8,232,047.

(60) Provisional application No. 60/853,916, filed on Oct. 24, 2006.

(51) Int. Cl.
*C12Q 1/25* (2006.01)
*C12Q 1/66* (2006.01)

(52) U.S. Cl.
CPC ..... *C12Q 1/66* (2013.01); *G01N 2333/90241* (2013.01)

(58) Field of Classification Search
CPC ..... C12Q 1/66
See application file for complete search history.

(56) References Cited

U.S. PATENT DOCUMENTS

| | | | | |
|---|---|---|---|---|
| 6,171,809 | B1 | 1/2001 | Roelant | |
| 7,537,912 | B2 | 5/2009 | Wood et al. | |
| 8,232,047 | B2 * | 7/2012 | Leu | C12Q 1/66 435/25 |
| 8,859,220 | B2 | 10/2014 | Hawkins et al. | |
| RE46,199 | E * | 11/2016 | Leu | C12Q 1/66 |
| 2006/0008860 | A1 | 1/2006 | Fan et al. | |

FOREIGN PATENT DOCUMENTS

| | | |
|---|---|---|
| JP | 08-047399 | 2/1996 |
| JP | 2005-515977 | 6/2005 |
| JP | 2005-245342 | 9/2005 |
| JP | 2006-517401 | 7/2006 |
| WO | 00/18953 | 4/2000 |
| WO | 01/55446 | 8/2001 |
| WO | 03/044223 | 5/2003 |
| WO | 2006/061906 | 6/2006 |
| WO | 2006/085972 | 8/2006 |
| WO | 2006/096735 | 9/2006 |
| WO | 2006/121331 | 11/2006 |
| WO | 2006/130551 | 12/2006 |

OTHER PUBLICATIONS

International Search Report PCT/AU2007/001615, dated Dec. 13, 2007 (3 pages).
Written Opinion PCT/AU2007/001615, dated Dec. 13, 2007 (7 pages).
International Preliminary Report on Patentability PCT/AU2007/001615, completed Dec. 19, 2008 (8 pages).
Supplementary European Search Report 07815420.0-2401 dated May 12, 2010 (7 pages).
Communication, EP07815420.0-1404, dated Mar. 20, 2013 (4 pages).
Communication, EP07815420.0-1404, dated Oct. 1, 2013 (3 pages).
Communication, EP07815420.0-1404, dated Apr. 14, 2014 (3 pages).
Patent Examination Report No. 1, AU2007308745, dated Jul. 17, 2012 (2 pages).
Notice of Rejection, English Summary JP2009-533610 dated Mar. 19, 2013 (8 pages).
Notice of Rejection, English Summary JP2009-533610 dated May 27, 2014 (3 pages).
Notification of Defects, English Translation IL198355 dated May 6, 2012 (1 page).
Notification of Technical Defects Prior to Allowance, English Translation IL198355 dated Nov. 19, 2013 (3 pages).
Notice of Office Action, KR10-2009-7010509, dated Feb. 27, 2014 (6 pages).
Rodionova and Petushkov. Effect of different salts and detergents on luciferin-luciferase luminescence of the enchytraeid *Fridericia heliota*, J. Photochemistry and Photobiology B: Biology, 83 (2006) 123-128.
Markova et al. Cloning and Expression of cDNA for a Luciferase from the Marine Copepod *Metridia longa*. J. Biol. Chem. 279 (2004) 3212-3217.
Gerasimova and Kudryasheva. Effects of potassium halides on bacterial bioluminescence, J. Photochemistry and Photobiology B: Biology 66 (2002), 218-222.
Bhaumik and Gambhir. Optical imaging of *Renilla* luciferase reporter gene expression in living mice. Proc. Nat. Acad. Sci. 99 (2002) 377-382.

(Continued)

*Primary Examiner* — Johnny F Railey, II
(74) *Attorney, Agent, or Firm* — Thompson Hine LLP

(57) ABSTRACT

Reagents and compositions for use in reactions catalysed by luciferase enzymes, and in particular for use in luciferase-based gene reporter assays are described. The invention also provides methods and compositions for, inter alia, increasing the sensitivity and/or improving the kinetics of luciferase-catalysed reactions.

19 Claims, 30 Drawing Sheets

(56) References Cited

OTHER PUBLICATIONS

Petushkov and Rodinova. Purification and partial spectral characterization of a novel luciferin from the luminous enchytraeid *Fridericia heliota*. J. Photochem Photobiol B 87(2007), Abstract Only.
Marques et al. LC-MS and microscale NMR analysis of luciferin-related compounds from the bioluminescent earthworm *Fridericia heliota*. J. Photochem. Photobio B 102 (2011) , Abstract Only.
Gonzalaz. Synthesis, Luminescence, and Applications of Coelenterazine and its Analogs (2007), 8 pages, available at http://www.chemistry.illinois.edu/research/organic/seminar_extracts/2006_2007/03GonzalezFINALAbstract.pdf.
JAPIO On-line Abstract, Accession No. 1996-047399 of JP 08047399 A (Eiken Che, Co. Ltd.) Feb. 20, 1996.

* cited by examiner

LUCIFERASE SIGNAL ENHANCING COMPOSITIONS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*RELATED APPLICATIONS*

*This is an application for reissue of U.S. Pat. No. 8,232,047 entitled LUCIFERASE SIGNAL ENHANCING COMPOSITIONS issued on Jul. 31, 2012 by Marco Peter Leu and John Michael Daly, and is a divisional of application Ser. No. 14/447,935, which is also an application for reissue of U.S. Pat. No. 8,232,047.*

*Notice: More than one reissue application has been filed for the reissue of U.S. Pat. No. 8,232,047. The reissue applications are the present application, and Ser. No. 14/447,935, all of which are divisional reissues of U.S. Pat. No. 8,232,047.*

FIELD OF THE INVENTION

The present invention relates generally to reagents and compositions for use in reactions catalysed by luciferase enzymes, for example in luciferase-based gene reporter assays and applications in which luciferase enzymes are utilised as a detectable and/or quantifiable label bound to a molecule such as antibodies for immunocytochemical assays or enzyme-linked immunosorbent assays (ELISA). The invention also provides methods and compositions for, inter alia, increasing the sensitivity and/or improving the kinetics of luciferase-catalysed reactions.

BACKGROUND OF THE INVENTION

Reporter gene assays represent an important tool in studies of gene expression, permitting an understanding of what controls the expression of a gene of interest e.g., DNA sequences, transcription factors, RNA sequences, RNA-binding proteins, signal transduction pathways and specific stimuli. In particular, reporter assays can be used to identify nucleic acid regions important in gene regulation. Such regions and/or the factors that bind or modulate them may serve as potential targets for therapeutic intervention in the treatment or prevention of human diseases. Reporter assays can also be used to screen drugs for their ability to modify gene expression.

Typically reporter assays are used to identify a gene promoter region or specific elements within a promoter, such as transcription factor binding sites or other regulatory elements. Alternatively, such assays are used to study the response of a promoter or regulatory element to various stimuli or agents. In some applications, the reporter constructs used in the assay, or transfected cells, are introduced into an organism to study promoter function in vivo. Further, reporter assays can be used to study or measure signal transduction pathways upstream of a specific promoter.

By way of example, in the case of reporter assays designed to investigate putative promoter sequences or other transcriptional regulatory elements, nucleic acids to be interrogated are cloned into reporter plasmids in a location so as to permit the regulation of transcription of a downstream reporter gene, and thus expression of a reporter protein encoded by the reporter gene. The reporter protein should be distinguishable from endogenous proteins present in the cell in which the reporter plasmid is transfected for ease of detection, and preferably expression of the reporter protein should be readily quantifiable. The reporter protein is quantified in an appropriate assay and often expressed relative to the level of a control reporter driven by a ubiquitous promoter such as, for example, the promoter SV40. The control reporter must be distinguishable from the test reporter and is generally contained on a separate vector that is co-transfected with the test vector and used to control for transfection efficiency. Such assays are based on the premise that cells take up proportionally equal amounts of both vectors.

A variety of different applications for gene reporter assays involve measuring a change in gene expression over time or after addition of a compound, such as a drug, ligand, hormone etc. This is of particular importance in drug screening. Following the addition of the drug, detecting a measurable change in levels of the reporter protein may be delayed and diluted as changes in expression levels are transmitted through mRNA to protein. A significant advance in such applications recently made by the present applicant is the combined use of mRNA- and protein-destabilizing elements in the reporter vector to improve the speed and magnitude of response, as described in co-pending U.S. patent application Ser. No. 10/658,093, the disclosure of which is incorporated herein by reference.

Various reporter gene assay systems are commercially available utilising different detectable reporter proteins, the most common being chloramphenicol transferase (CAT), β galactosidase (β-gal), secreted alkaline phosphatase, and various fluorescent proteins and luciferases.

Luciferase is the most commonly used reporter protein for in vitro assay systems. Luciferases are enzymes capable of bioluminescence and are found naturally in a range of organisms. In commercially available assay systems, luciferases can be divided into those which utilise D-luciferin as a substrate and those which utilise coelenterazine as a substrate. The most widely employed example of the former is firefly luciferase, an intracellular enzyme. Additional examples of luciferases utilising D-luciferin include other members of Coleoptera, such as click beetles and railroad worms. Luciferases may also be distinguished on the basis of whether the organism from which they are derived is terrestrial or aquatic (typically marine). Luciferases utilising coelenterazine as a substrate are typically derived from marine animals such as the soft coral Renilla or the copepod Gaussia, whereas D-luciferin-utilising luciferases are typically derived from terrestrial animals. A further means of distinguishing luciferases is on the basis of whether they are secreted or non-secreted in their native state; i.e. in the organism from which they are derived. Luciferases derived from terrestrial organisms are typically non-secreted (intracellular), whilst those derived from marine organisms may be secreted or non-secreted (intracellular). For example, Renilla luciferase is intracellular, whereas Gaussia luciferase in its native state is a secreted enzyme. The secretion of luciferases by marine organisms is thought to be a protective response designed to distract approaching predators. Other secreted luciferases include those from Metridia longa, Vargula hilgendorfii, Oplophorus gracilirostris, Pleuromamma xiphias, Cypridina noctiluca and other members of Metridinidae. Vargula luciferase utilises a substrate that is different to coelenterazine or D-luciferin. Another class of luciferase is those derived from dinoflagellates.

Luciferase-based assay systems may employ more than one luciferase, typically of different origin and each utilising a different substrate, enabling both test and control reporter to be measured in the same assay. By way of example, a putative promoter element is cloned upstream of a firefly luciferase reporter gene such that it drives expression of the luciferase gene. This plasmid is transiently transfected into a cell line, along with a control plasmid containing the Renilla luciferase gene driven by the SV40 promoter. First luciferin is added to activate the firefly luciferase, activity of this reporter is measured, and then a "quench and activate" reagent is added. This "quench and activate" reagent contains a compound that quenches the luciferin signal and also contains coelenterazine to activate the Renilla luciferase, the activity of which is then measured. The level of firefly luciferase activity is dependent not only on promoter activity but also on transfection efficiency. This varies greatly, depending on the amount of DNA, the quality of the DNA preparation and the condition of the cells. The co-transfected control plasmid (Renilla luciferase driven by a suitable promoter such as the SV40 promoter) is used to correct for these variables, based on the premise that Renilla luciferase activity is proportional to the amount of firefly luciferase-encoding plasmid taken up by the cells. Alternatively or additionally, the Renilla luciferase may be used to control for other variables, such as cell number, cell viability and/or general transcriptional activity; or may be used to determine whether a particular treatment or compound applied to the cells affects both promoters or is specific to one of them.

Luciferase-based assay systems, in particular those utilising one or more intracellular luciferases, often employ two buffers, a lysis buffer and an assay buffer. The lysis buffer is added to the cells first to lyse the cells and thus release luciferase, facilitating subsequent measurement. An assay buffer containing the luciferase substrate and any cofactors is then added, after which measurement of luciferase activity is taken. Measurement may be made immediately (i.e. within seconds) of the addition of the assay buffer (so-called "flash" reaction), or minutes or hours later (so-called "glow" reactions) by using "glow" reagents in the assay buffer that keep the light signal stable for an extended period of time. Flash reactions provide the highest signal strength (light units per second) and thereby have the advantage of providing the highest sensitivity. Glow reactions are particularly advantageous in applications where, for example, the user does not have a suitable luminometer (equipped with injectors) readily available or in some high throughput screening applications where batch-processing requires a delay between injection and measurement.

Secreted luciferases are measured in samples of the conditioned medium surrounding the test cells. As such, lysis buffers are not used with secreted luciferases.

There are a number of disadvantages associated with existing buffers and reagents for luciferase reporter assays.

In particular, there is a need for reagents, reaction compositions and kits that provide improved sensitivity in luciferase reactions; that is, a signal strength of greater intensity than is achievable with existing reagents. This is of particular relevance where the reporter gene assayed provides only low levels of luciferase in the cells of interest, for example, where the promoter being studied has only low activity, and/or where the cells of interest are difficult to transfect/transduce with the reporter vector. Increased sensitivity would also facilitate the miniaturization of reporter assays by reducing the minimum number of cells required to yield a signal strength that can be reliably measured.

When utilizing assay systems including destabilizing elements such as those described in co-pending U.S. patent application Ser. No. 10/658,093, the steady-state luciferase signal is reduced. Thus reagents that provide higher signal strength would be particularly advantageous for reporter assay systems utilizing destabilizing elements.

Furthermore, there is currently a compromise between "flash" and "glow" buffers and reagents. That is, to obtain an intense flash, the glow phase is sacrificed and vice versa. There is a clear need for buffers and reagents that can provide a high sensitivity flash reaction but also provide a prolonged glow. Buffers facilitating the generation of both high flash and prolonged glow from luciferase-catalysed bioluminescence reactions would provide the user with a dual purpose reagent that can provide high sensitivity (flash reactions) where needed but also provide the convenience of glow reactions for applications where high sensitivity is not required.

Finally, to enable simultaneous measurement of two or more different luciferases based on differences in the wavelength of emission, it is necessary to have a single reagent capable of supporting the activity of the two or more different luciferases.

SUMMARY OF THE INVENTION

The present invention provides reagent compositions, and kits comprising such compositions, for use in determining the amount or activity of a luciferase enzyme in a sample. The present invention further provides methods for using the reagent compositions and for determining the amount or activity of a luciferase enzyme in a sample The present invention is predicated, in part, on the inventors' surprising findings that various modifications of reagent compositions can have profound impact on the activity of certain classes of luciferase enzymes and on the development of novel reagent compositions which permit, inter alia, the generation of higher sensitivity (stronger flash phase), a reduced rate of luminescent signal decay (a more stable glow phase), reduced lysis time and/or assay time, and improved stability of enzymatic activity or potential over time than is achievable using currently available compositions.

In particular, the inventors have discovered that luciferases that are secreted in their native form have properties that are distinct from the more typically used intracellular luciferases and as such have quite distinct requirements with respect to reagent compositions. Moreover, when these normally secreted luciferases are expressed intracellularly, the inventors discovered that they become unsuitable for use with any currently available reagent compositions. The inventors subsequently identified the key features and components required to make reagents that are suitable for use with such luciferases when used alone or in combination with a different class of luciferase.

In a first aspect, the present invention provides a reagent composition for use in determining the amount and/or activity of luciferase in a sample, wherein the reagent composition permits generation of an enhanced luminescent signal, a reduced rate of luminescent signal decay from the luciferase and/or improved stability of luciferase activity over time in cell lysates. Typically, in the presence of the luciferase, the reagent composition provides an environment suitable to facilitate conversion of the luciferase into an active conformation.

The luciferase may be secreted or non-secreted and may be derived from a luciferase that is secreted or non-secreted in its native form. In an embodiment the luciferase is derived from a luciferase that is secreted in its native form. In a particular embodiment the luciferase is a non-secreted luciferase that is a modified form of a luciferase which is secreted in its native form. The non-secreted luciferase may be expressed in the cytoplasm or other cellular compartment, typically wherein the cellular compartment provides a reducing environment.

The luciferase may utilise any known luciferase substrate, such as, for example, luciferin or coelenterazine. In one embodiment, the luciferase utilises coelenterazine as substrate and is of marine origin. The luciferase of marine origin may be derived, for example, from Gaussia spp., Pleuromamma spp., Metridia spp., Cypridina spp. or Oplophorus spp. The luciferase may be a variant or derivative of a naturally occurring luciferase.

The reagent composition may comprise one or more chelators, bromide anions, a non-ionic detergent at a concentration of less than 1% or a zwitterionic detergent, at least one oxidising agent or combination of oxidising and reducing agents, and/or have a pH of above about 8.

Typically the chelator is a divalent metal chelator. The divalent metal chelator may, for example, be selected from EDTA, CDTA and EGTA. In one embodiment, the divalent metal chelator is EDTA, present at a concentration of at least 0.1 mM, more preferably between about 1 mM and 30 mM, more typically between about 4 mM and about 15 mM.

The detergent may be a zwitterionic or more preferably a non-ionic, detergent. The detergent is preferably at a final concentration of less than about 1%. In one embodiment, the detergent may be present at a concentration of between about 0.05% and about 0.2% when first contacted with the sample or cell. The detergent may be selected from, for example, Triton X-100, NP101 or NP40. In a particular embodiment the detergent is NP40.

Typically the oxidising agent or combination of oxidising and reducing agents result in oxidation of the luciferase thereby facilitating the adoption of an active conformation by the luciferase. The reducing agent may comprise a thiol group. In a particular embodiment, the composition comprises a redox buffer combination such as a mixture of oxidised and reduced glutathione.

Typically the reagent composition has a pH of above about 8, more typically between about 8 and about 9, or more typically between about 8.4 and 8.8.

The bromide anions may be provided in the form of one or more bromide salts. The bromide salts may be, for example, sodium bromide, potassium bromide or rubidium bromide. Typically the bromide anion is present at a concentration of at least about 1 mM, generally between about 1 mM and about 500 mM.

In a second aspect the present invention provides a reagent composition for determining the amount and/or activity of a recombinant luciferase in a sample, the reagent composition comprising one or more chelators, wherein the recombinant luciferase is a non-secreted variant of a luciferase that is secreted in its native form.

The chelator may be a divalent metal chelator. The chelator may, for example, be selected from EDTA, CDTA and EGTA. In one embodiment, the divalent metal chelator is EDTA, present at a concentration of at least 0.1 mM, more preferably between about 1 mM and 30 mM, more typically between about 4 mM and about 15 mM.

The reagent composition may further comprise bromide anions, a non-ionic detergent at a concentration of less than 1% or a zwitterionic detergent, at least one oxidising agent or combination of oxidising and reducing agents, and/or have a pH of above about 8.

The reagent composition may further comprise the luciferase substrate.

In a third aspect the present invention provides a reagent composition for determining the amount and/or activity of a recombinant luciferase in a sample, the reagent composition comprising bromide anions, wherein the recombinant luciferase is a non-secreted variant of a luciferase that is secreted in its native form.

The bromide anions may be provided in the form of one or more bromide salts. The bromide salts may be selected from sodium bromide, potassium bromide or rubidium bromide. Typically the bromide anion is present at a concentration of at least about 1 mM, generally between about 1 mM and about 500 mM.

The reagent composition may further comprise one or more chelators, a non-ionic detergent at a concentration of less than 1% or a zwitterionic detergent, at least one oxidising agent or combination of oxidising and reducing agents, and/or have a pH of above about 8.

The reagent composition may further comprise the luciferase substrate.

In a fourth aspect the present invention provides a method for determining the amount and/or activity of luciferase in a cell or sample of cells, the method comprising:

(a) providing cells expressing luciferase and wherein the luciferase is predominantly or totally present in an inactive state or conformation;

(b) incubating the cells with an effective amount of a reagent composition capable of converting the luciferase from an inactive state or conformation to an active state or conformation;

(c) adding a substrate of the luciferase enzyme, and optionally cofactors required for bioluminescent activity of the luciferase, such as CoA, ATP and magnesium; and (d) detecting the bioluminescent signal generated by the active luciferase.

Typically, the composition for converting the luciferase from an inactive state or conformation to an active state or conformation provides a chelator and/or a redox environment suitable for conversion of the luciferase into an active conformation. The redox environment may be suitable for or enable oxidation of the luciferase. Additionally, the reagent composition may comprise one or more of bromide anions, a non-ionic detergent at a concentration of less than 1% or a zwitterionic detergent, at least one oxidising agent or combination of oxidising and reducing agents, and have a pH of above about 8.

The reagent composition may be a composition of any one of the first to the third aspects. The reagent composition may further comprise the luciferase substrate.

The luciferase may be a recombinant luciferase that is a non-secreted variant of a luciferase that is secreted in its native form.

In a fifth aspect, the present invention provides a method for determining the amount and/or activity of a recombinant luciferase in a cell or sample of cells, the method comprising:

(a) lysing the cell or cells;

(b) contacting the cell lysate with an effective amount of a reagent composition comprising a chelator;

(c) adding a substrate of the luciferase enzyme, and optionally cofactors required for bioluminescent activity of the luciferase, such as CoA, ATP and magnesium; and (d) detecting bioluminescence in the sample;

wherein the recombinant luciferase is a non-secreted variant of a luciferase that is secreted in its native form.

The reagent composition may comprise a detergent, such that steps (a) and (b) may be combined in a single step. In certain embodiments, the reagent composition comprises the luciferase substrate such that steps (b) and (c) may be combined in a single step.

The reagent composition may be a composition of any one of the first to the third aspects.

In a sixth aspect present invention provides a method for increasing the bioluminescent signal generated by a luciferase enzyme, the method comprising contacting the luciferase with an effective amount of a reagent composition that provides an environment that enables or promotes conversion of the luciferase into an active state or conformation such as a suitable redox environment. Typically, the reagent composition comprises one or more of a bromide salt, a non-ionic detergent at a concentration of less than 1%, a divalent metal chelator, preferably at a concentration of at least 1 mM, at least one oxidising agent or combination of oxidising and reducing agents, and a pH of above about 8.

In a seventh aspect the present invention provides a method for increasing the bioluminescent signal generated by a luciferase enzyme, the method comprising contacting the luciferase with an effective amount of one or more divalent metal chelators. The divalent metal chelator may, for example, be selected from EDTA, CDTA and EGTA. In one embodiment, the divalent metal chelator is EDTA, present at a concentration of at least 0.1 mM, more preferably between about 1 mM and 30 mM, more typically between about 4 mM and about 15 mM.

In an eighth aspect the present invention provides a method for increasing the bioluminescent signal generated by a luciferase enzyme, the method comprising contacting the luciferase with an effective amount of bromide anions, typically in the form of a bromide salt.

In a ninth aspect the present invention provides a method of reducing the rate of decay of the bioluminescent signal generated by a luciferase enzyme, the method comprising contacting the luciferase with an effective amount of a reagent composition wherein the reagent composition provides an environment suitable to facilitate conversion of the luciferase into an active state or conformation, such as a suitable redox environment.

Typically the bioluminescent signal is prolonged during a phase beginning several minutes after addition of substrate.

In a tenth aspect the present invention provides a method of reducing the rate of decay of the bioluminescent signal generated by a luciferase enzyme, the method comprising contacting the luciferase with one or more divalent metal chelators. The divalent metal chelator may, for example, be selected from EDTA, CDTA and EGTA. In one embodiment, the divalent metal chelator is EDTA, present at a concentration of at least 0.1 mM, more preferably between about 1 mM and 30 mM, more typically between about 4 mM and about 15 mM.

In an eleventh aspect the present invention provides a method of reducing the rate of decay of the bioluminescent signal generated by a luciferase enzyme, the method comprising contacting the luciferase with an effective amount of bromide, typically in the form of a bromide salt.

Typically in accordance with the sixth to the eleventh aspects the luciferase is a recombinant luciferase that is a non-secreted variant of a luciferase that is secreted in its native form.

Also provided are methods for reducing the time required to achieve optimal or stable luciferase activity. Without being limited by any one theory or mode of action, the reduce time required to achieve optimal or stable luciferase activity may result from, or be associated with, reduced lysis time and/or assay time, and improved stability of enzymatic activity or potential over time.

In a twelfth aspect the present invention provides a kit for use in assaying the amount and/or activity of a luciferase, the kit comprising at least one reagent composition wherein the reagent composition provides an environment suitable to facilitate conversion of the luciferase into an active conformation.

The reagent composition may be a composition of any one of the first to the third aspects. The luciferase may be a recombinant luciferase that is a non-secreted variant of a luciferase that is secreted in its native form.

In a thirteenth aspect the present invention provides a kit for use in assaying the amount and/or activity of a luciferase, the kit comprising bromide ions and a luciferase substrate.

The luciferase may be a recombinant luciferase that is a non-secreted variant of a luciferase that is secreted in its native form.

In accordance with any one of the above aspects or embodiments, the reagent composition may further comprise an antioxidant. Optionally the composition further comprises BSA, protease inhibitors, glycerol, urea or a luciferase substrate.

In accordance with any one of the above aspects or embodiments, the reagent composition may be in the form of a buffer for lysing cells comprising the luciferase. Accordingly, the lysis buffer may further comprise additional components such as, for example, glycerol and protease inhibitors. The buffering agent may, for example, be Tris, Hepes or a phosphate buffer. The lysis buffer may be in the form of a combined cell lysis/luciferase assay buffer and accordingly, the composition may further comprise a luciferase substrate such as colenterazine.

Typically, in accordance with the above aspects and embodiments, the luciferase is expressed from a reporter gene and the amount or activity of luciferase is determined as part of a reporter gene assay. The reporter gene assay may be part of a multiple luciferase assay.

The invention also relates to a reagent composition for use in determining the amount and/or activity of luciferase in a sample, wherein in the presence of the luciferase, the reagent composition provides an environment suitable to facilitate conversion of the luciferase into an active state or conformation.

The luciferase may be a recombinant luciferase. The recombinant luciferase may be a non-secreted form of a luciferase that is secreted in its native form.

The reagent composition may provide a redox environment suitable to facilitate folding of the luciferase into an active conformation. The reagent composition may provide an environment suitable to facilitate disaggregation of the luciferase and/or separation from interfering proteins and/or unfolding of the luciferase in such a way as to facilitate subsequent refolding of the luciferase into an active state.

Typically the environment provided by the reagent composition facilitates a more rapid conversion of inactive luciferase to an active conformation or adoption or maintenance of a more active conformation. Alternatively or in addition, the environment may enhance the overall activity of luciferase in a sample by increasing the proportion of luciferase that adopts the most active conformation. Alternatively or in addition, the environment may facilitate the maintenance of a state of constant activity of the luciferase in the sample or reduce the time taken for the sample to reach a state of constant activity of the luciferase. Typically, this is achieved by reducing the time taken for the luciferase in the sample to reach its maximum activity.

The reagent composition may comprise a zwitterionic or more preferably a non-ionic, detergent. The detergent is preferably at a final concentration of less than about 1%. In one embodiment, the detergent may be present at a concentration of between about 0.05% and about 0.2% when first contacted with the sample or cell. The detergent may be selected from, for example, Triton X-100, NP101 or NP40. In a particular embodiment the detergent is NP40.

Alternatively or in addition, the reagent composition may comprise at least one suitable oxidising agent or a combination of oxidising and reducing agents. The agent(s) may comprise a thiol group. Typically the agent(s) results in oxidation of the luciferase thereby facilitating the adoption of an active conformation by the luciferase. In a particular embodiment, the composition comprises a redox buffer combination such as a mixture of oxidised and reduced glutathione.

Alternatively or in addition, the reagent composition may have a pH of above about 8, typically between about 8 and about 9, or more typically between about 8.4 and 8.8.

The reagent composition may further comprise one or more chelators such as divalent metal chelators. The chelator may, for example, be selected from EDTA, CDTA and EGTA. In one embodiment, the chelator is EDTA. Typically the chelator is present at a concentration of at least 0.1 mM, more preferably between about 1 mM and 30 mM, more typically between about 4 mM and about 15 mM.

The reagent composition may further comprise bromide anions, generally in the form of at least one bromide salt. The bromide salt may be, for example, sodium bromide, potassium bromide or rubidium bromide. Typically the bromide anion is present at a concentration of at least about 1 mM, generally between about 1 mM and about 500 mM.

The invention also relates to a method for determining the amount or activity of luciferase in a sample, the method comprising:

(a) incubating the sample with an effective amount of a reagent composition according to the invention;

(b) adding the luciferase substrate; and (c) detecting bioluminescence in the sample.

The substrate may be present in the reagent composition of step (a) or in a second composition, optionally also comprising cofactors required for bioluminescent activity of the luciferase, such as CoA, ATP and magnesium. The pH of the second reagent composition may be lower than the pH of the first composition.

BRIEF DESCRIPTION OF THE DRAWINGS

Embodiments of the present invention will now be described, by way of example only, with reference to the accompanying drawings.

DETAILED DESCRIPTION OF THE INVENTION

Figure 1:
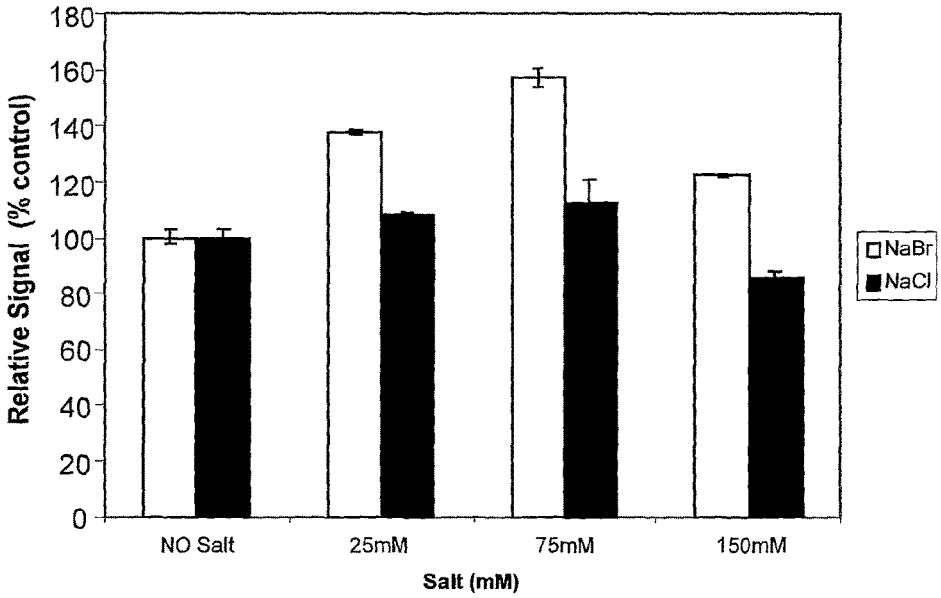
FIG. 1. shows the effect of bromide ions on the activity of secreted Gaussia luciferase expressed in HeLa cells.

Throughout this specification and the claims which follow, unless the context requires otherwise, the word "comprise", and variations such as "comprises" or "comprising", will be understood to imply the inclusion of a stated integer or step or group of integers or steps but not the exclusion of any other integer or step or group of integers or steps.

The articles "a" and "an" are used herein to refer to one or to more than one (i.e., to at least one) of the grammatical object of the article. By way of example, "an element" means one element or more than one element.

As used herein in the context of the conversion of a luciferase enzyme from one conformation to another, the term "facilitates" means that the reagent composition enables, produces, or promotes such conversion. Thus, facilitation of the conversion of luciferase into an active conformation may be passive or active, and direct or indirect. For example, the reagent composition may provide a suitable environment in which conversion of the luciferase into an active conformation may take place. Alternatively, the reagent composition may directly or indirectly promote or otherwise produce or generate such a conversion. An agent, additive or component of a reagent that "facilitates" conversion of a luciferase enzyme is typically one that provides for a more efficient conversion relative to a reagent that lacks the agent but is otherwise identical or substantially equivalent.

As used herein, the term "conversion" refers to the folding, disaggregation, re-folding or other modification of a luciferase enzyme in achieving an active state or conformation. Further reference to conversion of a luciferase into an active conformation is to be taken to mean either the conversion from an inactive state or conformation to an active state or conformation, or the conversion from a partially active or less active state or conformation to a more active state or conformation. In this context the term "conformation" refers to the structure (for example tertiary or quaternary structure) adopted by the enzyme and which correlates with the ability of the enzyme to catalyse a reaction and generate a bioluminescent signal upon addition of substrate. The actual catalytic activity of the luciferase does not occur in the absence of substrate. However, a luciferase that has been converted to a more active state or conformation will be capable of generating more luminescence once the substrate is added than would be possible in the absence of such conversion. This increased luminescence would typically be evident in a flash reaction, which is to say that the conversion of a luciferase to an active format is a separate process to the enablement of a prolonged glow by, for example, blocking a negative feedback mechanism that effectively reduces the activity of the luciferase subsequent to its initial catalytic activity in the presence of substrate.

The term "enhanced" as used herein in the context of the bioluminescent signal intensity of a luciferase means enhanced or increased, qualitatively or quantitatively, signal intensity relative to that achieved in the absence of the reagent composition and/or in the presence of a composition of the prior art. Similarly, the term "reduced rate of decay" is used to indicate a rate of decay of bioluminescent signal in the absence of the reagent composition and/or in the presence of a composition of the prior art.

As used herein the term "effective amount" includes within its meaning a non-toxic but sufficient amount of a reagent composition to provide the desired effect. The exact amount required may vary from case to case depending on factors such as the nature of the sample to be analyzed, the luciferase enzyme used and whether the luciferase is intracellular or secreted, and the constitution of the reagent or composition used. Thus, it is not possible to specify an exact "effective amount". However, for any given case, an appropriate "effective amount" may be determined by one of ordinary skill in the art using only routine experimentation.

As used herein the term "non-secreted luciferase" means a luciferase that is not exported or secreted from a cell into the extracellular environment. Thus "non-secreted" includes a luciferase retained in the cell in any form, and thus the luciferase may be cytoplasmic or membrane-associated. Typically, although not exclusively, where a luciferase is referred to herein as being a "non-secreted" form of a luciferase that is secreted in its native form, this secretion and absence of secretion refers to eukaryotic cells.

As used herein with reference to luciferase enzymes, the term "substrate" means the substrate molecule upon which the luciferase acts, excluding any additional cofactors that may be beneficial to, or required for, binding of the luciferase to the substrate and/or catalysis. For example, luciferase catalysed reactions may require or benefit from cofactors such as magnesium, CoA and ATP, however in the context of the present invention such cofactors are not considered to fall within the scope of the term "substrate". Luciferase "substrates" include for example D-luciferin and coelenterazine. For the purposes of the present application the term "luciferin" refers to the substrate D-luciferin and its analogues, which molecules are substrates for luciferases derived from, for example, Coleoptera such as firefly, click beetles and railroad worms. The term luciferin does not encompass coelenterazine, which represents a different luciferase substrate utilized by a distinct class of luciferase (such as those derived from Renilla, Gaussia and Metridia for example).

As disclosed herein, the inventors have developed reagent compositions enabling improved luciferase reporter systems demonstrating inter alia enhanced signal strength (stronger flash phase), a reduced rate of luminescent signal decay (a more stable glow phase), reduced lysis time and/or assay time, and improved stability of enzymatic activity or potential over time. Such systems find application in any luciferase-based reaction where it is desirable to determine or quantify the amount and/or activity of the luciferase enzyme. For example, compositions in accordance with embodiments of the invention are particularly, but not exclusively, applicable for use in conjunction with gene reporter assay systems, including those utilising destabilizing elements so as to provide a rapid response in addition to high signal strength. In addition, reagent compositions of the invention also find application in other assay systems wherein the amount and/or activity of one or more luciferase enzymes are to be determined. For example, the luciferase may be used as a reporter in an immunoassay or nucleic acid hybridisation assay and thus may be linked to, for example, an antibody or nucleic acid probe. Thus the luciferase may be a reporter or detectable label.

As disclosed and exemplified herein the inventors have elucidated unique properties of a particular class of luciferase enzyme; those that are secreted in their native state. The performance of such luciferases in luciferase assays can be substantially improved by using the reagent compositions and methods of the present invention. Furthermore, the inventors have discovered that when such luciferases are modified so as to prevent secretion and provide intracellular expression in target cells, the activity of the modified luciferase is markedly reduced, but can be quickly recovered by using reagent compositions and methods of the invention. In this context, the inventors have developed methods and reagent compositions that enable the use of luciferase proteins so modified in a variety of luciferase-catalysed reactions.

As disclosed herein the inventors have discovered that when a normally secreted luciferase is modified for intracellular expression and expressed in cells such as eukaryotic cells, the activity of the modified luciferase within the live cells is substantially reduced. Following lysis of the cells, the activity remains low but partially recovers over time, albeit very slowly. This poses a number of problems for the use of such modified luciferases in luciferase assays and in effect has prevented their successful commercialisation. The reduced enzymatic activity causes a reduction in bioluminescent signal strength. Longer incubation times (prior to adding substrate to initiate the reaction) provide some improvement to signal strength but also lengthen the time required to complete an assay. However the present inventors have discovered that even using long incubation times, the activity of the modified luciferase continues to increase, such that the entire assay becomes inaccurate and time-dependent. That is, luciferase activity is used as a measure of the amount of luciferase protein present in the sample such that it is necessary for each sample to contain the same activity per unit of luciferase protein. However in the case of these modified luciferases the lack of stability of the cell lysates with respect to luciferase activity prevents this, thereby rendering the assay inaccurate. Whereas some luciferases show decreased activity over time in cell lysis buffer (e.g. due to protease activity), the modified forms of normally secreted luciferases show substantial increases over time, representing an entirely new hurdle to be overcome if such modified luciferases are to be successfully exploited.

As disclosed and exemplified herein, the present inventors have for the first time identified components, additives or agents that when contacted with a cell lysate substantially improve the rate and efficiency at which the modified form of a normally secreted luciferase regains its activity or enzymatic potential. As identified herein and in accordance with particular embodiments of the invention, examples of such components include chelators, bromide ions, buffers with relatively high pH (e.g. above 8) and oxidising agents and/or a redox buffer. In the presence of such agents the luciferase achieves a high level of activity quickly and thereafter maintains a constant activity. This provides numerous benefits including shorter assay time (reduced time required in lysis buffer), higher sensitivity (greater maximal signal) and improved accuracy (signal less dependent on lysis time on sample-to-sample variations in efficiency of conversion to active form).

It is also shown herein that the activity of luciferases that are normally secreted, whether expressed in their native secretable state or modified for intracellular expression, is increased in the presence of bromide ions and decreased in the presence of detergent.

Reagent compositions of the present invention provide improved kinetics of luciferase-catalysed reactions. In particular, as disclosed herein, it has been found that using reagent compositions of the invention, very high bioluminescent signal strength in the first few seconds following addition of substrate can be coupled with a prolonged measurable bioluminescent signal (so-called "glow" reaction) for example at least about 10 minutes after initiation. During this "glow" period the signal strength declines only very slowly.

Components of reagent compositions of the invention which alone or in combination contribute to the improved kinetics include bromide salts, divalent metal chelators, high pH (at least about 8 or higher) and oxidizing agents, such as a mixture of reduced and oxidized glutathione. Reagent compositions can also include numerous additional components as will be readily appreciated and ascertained by those skilled in the art.

As exemplified herein, various modified cell lysis buffer compositions, for example including a bromide salt and/or reduced levels of detergent, provided very high signal strength when used with a modified intracellular Gaussia or Metridia luciferase, compared to the same luciferase used with commercially available Renilla or Gaussia assay reagents. This is the first demonstration that the high signal strength of a secreted luciferase can be combined with the rapid response dynamics of a destabilized intracellular luciferase in the form of a modified intracellular form of an enzyme which is secreted from the cell in its native form. Without wishing to be bound by theory, these data suggest that the high signal strength of secreted luciferases is not entirely dependent on their secreted state nor is it due simply to accumulation of high luciferase protein levels in the cell culture medium. Rather, the high signal strength appears to be at least partially due to an inherent ability of these enzymes to efficiently catalyse a rapid oxidation of substrate under appropriate conditions.

Reagent compositions of the present invention provide high bioluminescent signal strength and prolonged duration (equating to a reduced rate of decay) of bioluminescent signal when compared with presently available compositions. Without wishing to be bound by theory, it is considered that reagent compositions according to embodiments of the invention may provide an environment suitable for converting the luciferase from an inactive state or conformation into an active state or conformation. The change in conformation may comprise a change in protein folding and/or a change in redox state of the luciferase. Further, the conformational change may comprise the formation of one or more disulphide bridges in the luciferase protein. A change in state or conformation of a luciferase enzyme may be desired or required in a number of circumstances. For example, the luciferase may be expressed cytoplasmically as an inactive or partially inactive protein. In such instances, the luciferase may be a modified non-secreted form of a luciferase that is secreted in its native form.

In one embodiment, a reagent composition of the invention comprises at least one bromide anion or salt, for example sodium bromide, potassium bromide or rubidium bromide. The concentration of bromide salt may be between about 1 mM and about 500 mM. In one embodiment the concentration is between about 75 mM and about 225 mM. Typically the bromide anion is present at a concentration of at least about 1 mM, 2 mM, 5 mM, 10 mM, 20 mM, 50 mM, 75 mM, 100 mM, 150 mM, 200 mM, 250 mM, 300 mM, 400 mM or 500 mM.

A reagent composition of the invention may comprise a non-ionic detergent at a concentration of less than about 1%. The non-ionic detergent may be present at a concentration of less than about 0.5%, 0.4%, 0.3%, 0.2%, 0.15% or 0.1%. A reagent composition of the invention may comprise a zwitterionic detergent. In some embodiments, in particular in the case of reactions and assays utilising Gaussia and Metridia luciferases which are inhibited by detergent in a dose dependent manner, it is desirable to employ the minimum concentration of detergent required to achieve cell lysis. Accordingly, in one embodiment the suitable concentration of detergent is between about 0.05% and about 0.1%. The non-ionic detergent may be selected from, for example, Triton X-100, NP101 or NP40. In a particular embodiment the detergent is NP40. The zwitterionic detergent may be CHAPS.

However those skilled in the art will readily appreciate that where cell lysis is required or desired in order to practice an embodiment of the invention, cells may be lysed by any one or a number of techniques well known in the art. Many of such techniques do not require the use of detergents, but rather cell lysis may be achieved by, for example, sonication, osmotic pressure or other physical pressure. Thus reagent compositions and methods of the invention are not limited to any one particular means of cell lysis.

A reagent composition of the invention may have a pH of at least about 8, typically between about 8 and about 10, between about 8 and about 9, or between about 8.4 and about 8.8. Suitably, the pH may be at least about 8.1, 8.2, 8.3, 8.4, 8.5, 8.6, 8.7 or 8.8.

A reagent composition of the invention may comprise at least one oxidising agent or a combination of oxidising and reducing agents. Where a combination of oxidising and reducing agents is used, the relative proportions of the agents is typically such that the environment generated in the presence of the luciferase is an oxidising environment when compared with the cytosol of the cell expressing the luciferase. The composition may comprise a 'redox buffer combination' such as a mixture of oxidised and reduced glutathione. Redox pairs that exist and operate within normal eukaryotic cells are disclosed, for example, in Table 7 of [Foyer, C. H. (2005); The Plant Cell Vol 17:1866-1875]. Examples of redox pairs include: $O_2/H_2O$; $H_2O_2/OH^-$; NAD(P)/NAD(P)H; $TRX_{ox}/TRX_{red}$; cysteine/cystine; cysteamine/cystamine and DHA/ASC. Redox buffers may comprise a mixture of an oxidised form of a thiol (such as a disulphide dimer) and a reduced form. The reduced and oxidised thiols may be the same or different.

In a general sense, oxidation-reduction (redox) reactions are characterized by a change in oxidation number, usually by a transfer of electrons. The term "oxidation" typically refers to an increase in oxidation state or number (a loss of electrons). Whereas the term "reduction" refers to a decrease in oxidation state or number (a gain of electrons). An "oxidising agent" is sometimes referred to as an electron acceptor, and a "reducing agent" is sometimes referred to as a electron donor. Substances that have the ability to oxidize other substances are said to be "oxidative" and are referred to as "oxidising agents", "oxidants" or "oxidisers". Substances that have the ability to reduce other substances are said to be "reductive" and are referred to as "reducing agents", "reductants", or "reducers". Typically in a redox process, the reductant or reducing agent loses electrons and is oxidised and the oxidant or oxidising agent gains electrons and is reduced. One or more oxidizing agents and/or reducing agents may be present in a reagent composition or in a corresponding reaction mixture in which that reagent is used, in order to provide an overall "oxidising environment" or an overall "reducing environment" in that reagent or reaction mixture.

The oxidising agent or combination of oxidising and reducing agents may promote oxidation of the luciferase thereby promoting or otherwise facilitating the adoption of an active (or more active) conformation by the luciferase.

The oxidising agent or combination of oxidising and reducing agents may promote oxidation of the luciferase thereby promoting or otherwise facilitating the adoption of an active (or more active) conformation by the luciferase.

Those skilled in the art will appreciate that a variety of oxidising agents are suitable for the purposes of the present invention and are contemplated herein. For example, the oxidising agent may be a sulfhydryl group converting agent that contributes to the generation of an electrochemical potential in the reagent composition such that sulfhydryl groups are oxidised to disulphide bridges whilst the luciferase protein is not denatured. By way of example, the oxidising agent may be an agent capable of oxidising, directly or indirectly, thiol or cysteine thiol groups in the luciferase protein. As described herein reagent compositions of the invention may comprise a combination of oxidising and reducing agents. The oxidising agent may be an agent capable of oxidising, directly or indirectly, thiol or cysteine thiol groups in the luciferase protein, whilst the reducing agent may be an agent capable of reducing, directly or indirectly, thiol or cysteine thiol groups in the luciferase protein. For example, thiols, as reducing components of redox buffers, are known to affect the rates of thioldisulphide interchange reactions involved in protein folding. The redox buffer thiols can act as nucleophile, central thiol, or a leaving group. The overall rate of protein folding can be modulated by variation of the thiol component of a redox buffer.

A general equation describing the oxidation of thiols is shown in equation 1.0:

$$R—SH+R^1—SH \rightarrow R—S—S—R^1+2H^++2e^- \quad 1.0$$

The oxidising and reducing agents may be different compounds, or alternatively may be the oxidised and reduced forms of the same compound, e.g. the buffer may be comprised of a mixture of: $R^5$—SH (reduced form) and $R^5$—S—S—$R^5$ (oxidised form) or may, for example be comprised of: $R^6$—SH (reduced form) and $R^2$—S—S—$R^2$ (oxidised form).

One example of a suitable thiol for use in a redox buffer system is glutathione which is present as a thiol and a disulphide dimer. The glutathione redox buffer system uses the disulphide GSSG to provide oxidising equivalents and the monothiol GSH to generally catalyse disulphide bond isomerisation. The folding efficiency of an effective glutathione system generally has a solution potential similar to that of the endoplasmic reticulum ($E_{solution}$=−180 mV).

As generally described above, the GSH component of the GSH/GSSG buffer system can be replaced with other thiols. For example, the rate of in vitro folding of disulphide-containing proteins may be increased by utilising a small-molecule aromatic and aliphatic thiols. Monothiols with lower thiol pKa such as N-methylmercaptoacetamide (NMA) or 4-mercaptobenzoic acid form less stable disulphides and can be used at higher concentrations to give faster folding rates than glutathione. Generally, the leaving group ability of thiols is inversely correlated to the pKa of the thiol (Gough, J., D., J. Am. Chem. Soc., 2002, 124, 3885-3892; Gough, J., D., Bioorganic & Medicinal Chemistry Letters, 2005, 15, 777-781; Gough, J., G., Journal of Biotechnology, 2005, 115, 279-290; Gough, J., G., Journal of Biotechnology, 2006, 125, 39-47]. Examples of suitable small molecule aromatic thiols are shown below:

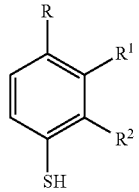

| R | R1 | R2 | Thiol pKa |
|---|---|---|---|
| $CH_2COOH$ | H | H | 6.6 |
| $CH_2OH$ | H | H | 6.5 |
| COOH | H | H | 6.95 |
| $SO_3H$ | H | H | 5.7 |
| $SO_2NHCH_2COOH$ | H | H | 5.2 |
| H | COOH | H | 6.3 |
| H | $CH_2COOH$ | H | 6.7 |
| H | H | COOH | 8.3 |
| H | H | $CH_2COOH$ | 7.2 |
| H | H | $COOC_2H_4OC_2H_4OC_2H_4OH$ | 6.9 |

The thiol concentration for aromatic thiols in redox buffer systems may vary considerably. The use of other aromatic thiols, such as 2,2'-[(4-mercaptophenyl)imino]bisethanol, in oxidation and thiol disulphide interchange reactions is known [DeCollo, T. V., J. Org. Chem., 2001, 66, 4244-4249].

Dithiols may also be used as a component of a redox buffer. In contrast to monothiols, dithiols can form cyclic disulphides and thus form less stable mixed disulphides. The addition of reduced dithiol (±)-trans-1,2-bis(mercaptoacetamido)cyclohexane (BMC or Vectrase-P) to a glutathione redox buffer may, for example, increase the rate and yield of folding of a protein. Moreover, using only covalent interactions, BMC can catalyse native disulphide bond formation, both in vitro and in vivo. Without wishing to be bound by theory, the second thiol of BMC may provide an intramolecular clock for substrate-induced thiol-disulphide exchange.

The oxidising agent may be an enzyme such as endoplasmic reticulum oxidoreductin 1 protein (Ero1p). Oxidative protein folding may involve both the oxidation of thiols and the isomerisation of non-native disulphide bonds. Accordingly, isomerase enzymes may also be used as part of a protein oxidising system. A suitable further component of an oxidative buffer is therefore protein disulphide isomerase (PDI) which has a role in catalysing the unscrambling of non-native disulphide bonds in proteins. Each PDI molecule has two active sites that contain the -Cys-Xaa-Xaa-Cys- sequence. Suitably, an enzymatic component of a redox buffer may contain the -Cys-Xaa-Xaa-Cys- sequence. Other enzymes that may be used, for example, in a redox buffer system include: thioredoxin, glutaredoxin and peroxiredoxin.

The isomerising component may be a mimic or an active fragment of an isomerase enzyme. Examples of active dithiol peptide fragments include the Cys-Xaa-Xaa-Cys tetrapeptide and the CysXaaCys tripeptide, wherein Xaa refers to any amino acid residue [Woycechowsky, K., J., Biochemistry, 2003, 42, 5387-5394]. For example, the tripeptide CysGlyCys (CGC) has been shown to have a disulphide reduction potential close to that of PDI. Another non-limiting example of a reducing agent suitable for use in a redox buffer for protein isomerisation and folding, and which is not a thiol derivative, is tris(2-carboxyethylphosphine) (TCEP) [Willis, M., S., Protein Science, 2005, 14, 1818-1826].

The oxidizing agent may be a mild oxidizing agent, suitable for oxidizing protein thiol groups, particularly cysteine thiol groups of the luciferase. The oxidizing agent may, itself, contain disulphide bridges and may be an amino acid derivative. The reducing agent may itself contain thiol groups and be an amino acid derivative.

Other suitable oxidising agents and methods include: molecular oxygen, metal ions, $Bu_3SnOMe/FeCl_3$, nitric oxide, halogens (e.g. bromine and iodine), sodium perbortate, borohydride exchange resin (BER)-transition metal salts system, a morpholine iodine complex, PCC, ammonium persulphate, $KMnO_4/CuSO_4$, $H_2O_2$, solvent free permanganate, PVP-$N_2O_4$ and cesium fluoride-Celite $O_2$ system, 2,6-dicarboxypyridinium chlorochromate (2,6-DCPCC) [Tajbakhsh, M., Tetrahedron Letters, 45, 2004, 1889-1893]; dimethylsulphoxide [Shad, S., T., A., Tetrahedron Lett., 2003, 44, 6789; Sanz, R., Synthesis, 2002, 856; Karimi, B., Synthesis, 2002, 2513]; laser prepared copper nanoparticles have been demonstrated to oxidise thiols to disulphides [Chen, T-Y, J. Phys. Chem. B, 2002, 106, 9717-9722]; electrochemical methods for the formation of disulphides: Leite, S., L., S., Synth. Commun., 1990, 20, 393 and Do, Q., T., Tetrahedron Letters, 1997, 38(19), 3383-3384]; manganese nodules [Parida, K., M., Journal of Colloid and Interface Science; 1998, 197, 236-241]; oxidation by soluble polymeric $MnO_2$ [Herszage, J., Environ. Sci. Technol., 2003, 37, 3332-3338]; molecular bromine on hydrated silica gel support [Ali, M., H., Tetrahedron Letters, 2002, 6271-6273]; oxidising polymers such as monochloro poly(styrenehydantoin) beads in water [Akdag, A., Tetrahedron Letters, 2006, 47, 3509-3510]; diamide; DTNB (5,5'-dithiobis(2-nitrobenzoic acid); hydrogen peroxide; N-methylmercaptoacetamide; sodium selenite (together with beta mercaptoethanol) [Rariy, R. V. & Klibanov A. M., (1997) Proc. Natl. Acad. Sci. USA 94: 13520-13523; Ferredoxin (reduced and oxidized); and Copper phenanthroline (Cu:phen) [Webb, T. I., Zang, Z., Lynch J. W. (2005) Proceedings of the Australian Physiological Society Vol 36: 44P].

A reagent composition of the invention may comprise one or more chelators. Suitable chelators include but are not limited to divalent metal chelators such as, for example, EDTA, CDTA and EGTA. The chelator may be present at any concentration but preferably at a concentration of between about 0.1 mM and about 50 mM, typically at a concentration of between about 0.1 mM and about 30 mM, more typically at a concentration of between about 0.1 mM and about 15 mM. The concentration may be at least about 0.1 mM, 0.2 mM, 0.5 mM, 1 mM, 2 mM, 3 mM, 4 mM, 5 mM, 7.5 mM, 10 mM, 12.5 mM or 15 mM.

Those skilled in the art will appreciate that where exemplary ranges or constituents are provided herein, these are not exhaustive but are merely illustrative of ranges and constituents that may be included in compositions of the invention in achieving rapid cell lysis or conversion of the luciferase to a more active state or conformation, enhanced bioluminescent signal intensity and/or prolongation of bioluminescent signal.

The findings, as exemplified herein, that bromide salts (including sodium bromide and potassium bromide) enhance activity of Gaussia and Metridia luciferases (in their native secreted form and as modified, intracellular enzymes) and that activity of both Gaussia luciferases and both Metridia luciferases is inhibited in the presence of detergent in a concentration dependent manner at detergent concentrations of less than 1% are particularly surprising in light of the previous dogma in the art that Gaussia and Metridia luciferase activity is sodium dependent and/or sensitive to cation concentration and is not inhibited by non-ionic detergents up to or above 2%.

Using reagent compositions of the invention, the bioluminescent signal generated by the luciferase can be prolonged during a "glow" phase that begins some minutes following addition of the luciferase substrate. For example, the bioluminescent signal can be prolonged during a phase that begins between about 3 minutes and about 15 minutes after addition of the substrate. Further, by way of example only, the bioluminescent signal generated by the luciferase may be such that starting from 10 minutes after initiation of the luciferase-catalysed reaction, the bioluminescent signal decays with a half-life of more than 20 minutes or more than 30 minutes.

The luciferase substrate may be a constituent of the reagent composition or may be independent. Where the luciferase substrate is not a constituent of the reagent composition, the substrate may be added to the sample containing luciferase either before, after or at the same time as addition of the reagent composition.

Typically luciferase-based reporter assay systems employ two buffers, a lysis buffer and an assay buffer (collectively referred to herein as "assay reagents"). The lysis buffer typically comprises components for lysing the cells containing the luciferase to be assayed while the assay buffer typically contains, inter alia, the substrate and any required cofactors for the luciferase reaction.

Reagent compositions of the present invention are typically in the form of cell lysis buffers. Advantageously, lysis buffers in accordance with the present invention effectively provide shorter lysis times than is possible with currently available buffers. Without wishing to be bound by theory, the present inventors suggest that these buffers provide a suitable environment for promoting or facilitating the folding or conversion of the luciferase to be assayed following cell lysis into an active state or conformation from an inactive state or conformation, or into a more active state or conformation from a less active state or conformation. Alternatively, reagent compositions of the invention may be in the form of a combined lysis and assay buffer such that only a single buffer composition is required to lyse cells, potentially directly within the medium in which the cells are cultured, and initiate the luciferase-catalysed reaction.

Reagent compositions in accordance with the present invention may typically be aqueous solutions, or alternatively may be in solid or dry form such as lyophilised. Whether aqueous or lyophilised, reagent compositions of the invention may be provided either comprising all constituents pre-mixed or as a combination of constituents to be mixed prior to use. The reagent composition may be used directly in an assay system for the determination of luciferase amount and/or activity, or may be reconstituted, dissolved, diluted or otherwise treated either chemically or physically such that the composition is capable of performing the desired function.

Reagent compositions of the present invention are applicable to determining the amount and/or activity of any luciferase in a sample. The luciferase may be a naturally occurring enzyme or modified enzyme. A naturally occurring luciferase may be derived from any one of a number of bioluminescent organisms, typically from the light organ thereof. Such organisms include but are not limited to bioluminescent bacteria, protozoa, coelenterates, molluscs, fish, flies, crustaceans and beetles. Conventionally, luciferases may be categorised according to the substrate utilised by the enzyme. One group of luciferases such as those of fireflies and click beetles utilise luciferin (D-luciferin). A second group of luciferases, such as those of the marine organisms Renilla, Gaussia, Pleuromamma, Metridia and Cypridina utilise coelenterazine. Other luciferases, such as Vargula luciferase, use a different substrate. The reagent compositions of the present invention are applicable to use with luciferases using luciferin or coelenterazine or any other substrates.

The reagent compositions of the invention are similarly applicable to use with either intracellular or secreted luciferases. Firefly and Renilla luciferases are intracellular in their natural state, whereas Gaussia and Metridia luciferases are secreted in their wild-type state. Gaussia luciferase is of particular interest as it has been shown to yield a bioluminescent signal strength higher than that achievable with Renilla luciferase and is the smallest known luciferase. Other secreted luciferases have also been shown to yield strong signal strength, for example Metridia longa luciferase.

The luciferase may be a variant or derivative of a naturally occurring luciferase. For example, the present invention finds particular application in reactions and assays involving modified, non-secreted forms of luciferases that are secreted in their native form. By way of example, a naturally secreted luciferase may be modified using standard molecular biological techniques by removal of signal sequences and/or fusion to an intracellular polypeptide such that the enzyme is no longer secreted but remains intracellular. Alternatively, or in addition, a number of other modifications well known to those in the art may be made, for example, to alter one or more amino acids in the luciferase polypeptide sequence to modulate expression and/or solubility of the enzyme in a cell culture system of choice. Such modulation may be an increase or decrease in expression and/or solubility, depending on the requirements of the particular application in which the luciferase, and the reagent compositions of the invention are to be employed. For example, it may be desirable to modify the luciferase by the introduction of one or more destabilising elements to destabilise the protein. Luciferases containing destabilising elements have shortened half-lives and are expressed at lower steady-state levels than luciferases which do not contain such elements. Suitable protein destabilising elements include PEST sequences (amino acid sequences enriched with the amino acids proline (P), glutamic acid (E), serine (S) and threonine (T)), a sequence encoding an intracellular protein degradation signal or degron, and ubiquitin. The enhanced sensitivity attained with reagent compositions of the present invention are particularly advantageous for use with destabilized luciferases given the lower steady state expression levels of such luciferases. Any suitable method for destabilising a protein is contemplated herein. Suitable methods are described, for example, in co-pending U.S. patent application Ser. No. 10/658,093 (the disclosure of which is incorporated herein by reference in its entirety). Expression of the luciferase may also be modified by, for example, the addition of sequences such as poly(A) tails, transcriptional or translational enhancers, and/or adapting codon usage in the encoding polynucleotide sequence for a particular expression system. For example, to optimise expression of the luciferase in insect cells or human cells, codon usage in the luciferase polynucleotide may be optimised for insect or human cells respectively. Approaches for codon usage adaptation and optimisation for different species are well known to those skilled in the art.

Further modifications that may be made to luciferase polypeptide or polynucleotide sequences are also well known to those skilled in the art. For example, restriction enzyme cleavage sites may be introduced into the polynucleotide, or the luciferase polypeptide may be fused or conjugated with a second polypeptide of different function such as a selectable marker (e.g. antibiotic resistance).

Those skilled in the art could readily predict using well know techniques such as computer modelling, those luciferases which are particularly amenable to use in accordance with the invention, as well as predict the modifications that may be made to a secreted luciferase the render the luciferase non-secreted. For example, luciferases that are secreted in their native form typically comprise cysteine residues that form disulphide bridges in the mature active conformation of the protein. The cysteine residues may be arranged in spacing patterns that are repeated within the amino acid sequence such that they can be predicted to form intramolecular disulphide bonds. Such luciferases typically show reduced activity when expressed intracellularly. Thus, those skilled in the art will appreciate that homologous luciferases sharing one or more of these characteristics of naturally secreted luciferases are particularly suitable for use in accordance with the present invention.

Suitable luciferases are readily obtainable by those skilled in the art using known techniques. The luciferase may be directly obtained from the light organ(s) of the bioluminescent organism. Alternatively the luciferase may be obtained from cultured cells, for example bacteria, yeast, insect cells or mammalian cells which have been transformed with nucleic acids encoding the luciferase.

When using secreted luciferases in in vitro reporter assays, a sample of the cell culture medium, rather than a cell lysate, is typically taken for measurement of luciferase activity. Whilst advantageous in some applications (e.g. repeated measurements from the same cells), secreted luciferases are not appropriate for other applications. In particular, the secreted luciferase accumulates in the cell culture medium such that rapid changes in gene expression can not be monitored accurately. Mutant, non-secreted forms of these luciferases (preferably containing destabilizing elements) overcome this limitation. One particular modified luciferase described herein is a modified Gaussia luciferase in which the 14 amino acid N-terminal signal peptide is deleted thereby generating a non-secreted luciferase. A second modified luciferase described herein is a modified Metridia luciferase in which the 17 amino acid N-terminal signal peptide is deleted thereby generating a non-secreted luciferase. Other secreted luciferases can be similarly modified for intracellular expression, particularly in eukaryotes, using a variety of methods well known to those skilled in the art.

In particular embodiments, reagent compositions of the present invention find application in reporter assay systems based on a luciferase, either intracellular or secreted, which utilises coelenterazine as a substrate or in dual luciferase reporter assays in which at least one of the luciferases utilises coelenterazine as a substrate and/or is secreted in its native form.

In accordance with the present invention, luciferase activity can be detected and measured by any one of a number of methods well known to those skilled in the art, including but not limited to using a luminometer, a scintillation counter, a photometer such as a photomultiplier photometer or photoemulsion film, or a charge-coupled device (CCD).

Reagent compositions of the invention provide improved kinetics of bioluminescence in luciferase reactions and offer advantages over the prior art. As such these compositions may be used in luciferase assays according to the invention, in preparing assay reagents and test kits according to the invention, and in standards and controls for assays and kits according to the invention. The present invention provides kits for carrying out assays of luciferase activity, such kits containing reagent compositions in accordance with the invention as described herein. Kits of the invention comprise, in one or more physical containers and typically packaged in a convenient form to facilitate use in luciferase assays, suitable quantifies of reagent compositions or constituents thereof for carrying out luciferase assays. Multiple reagent compositions, or various constituents of reagent compositions may be combined, for example in aqueous solution or lyophilised, in a single container or in multiple containers. Kits of the invention typically also comprise controls and standards to ensure the reliability and accuracy of assays carried out in accordance with the invention. Suitable controls and standards will be known to those skilled in the art.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The present invention will now be described with reference to the following specific examples, which should not be construed as in any way limiting the scope of the invention.

EXAMPLES

Part I

Luciferases

Example 1

Firefly luciferase and Renilla luciferase are the most commonly used luciferases in commercial luciferase-based reported systems. Although the secreted Gaussia luciferase and secreted Metridia luciferase provide higher sensitivity than firefly or Renilla luciferase, secreted luciferases accumulate in the culture medium and therefore are not ideal for reporter studies aimed at measuring temporal changes in gene expression.

To determine whether a mutant, non-secreted (and destabilized) version of a naturally secreted luciferase could provide the combined benefits of high signal strength and rapid response rates, the inventors cloned the Gaussia luciferase coding sequence into various RapidReporter plasmids (GeneStream) using a PCR strategy that deleted the 15 amino acid N-terminal signal peptide and fused the remaining Gaussia luciferase cDNA to N-terminal and C-terminal coding sequences that included sequences encoding protein destabilizing elements. The modified Gaussia luciferase is not secreted when expressed in mammalian cells. The precise intracellular location of the modified luciferase enzyme is assumed to be cytoplasmic. In the experiments described below, mammalian cells transfected with plasmids expressing either the native Gaussia luciferase (hereafter referred to as "secreted Gaussia luciferase") or the modified Gaussia luciferase (hereafter referred to as "non-secreted Gaussia luciferase") were lysed in the presence of a variety of lysis buffer compositions and bioluminescence measured.

To determine whether a second mutant, non-secreted (and destabilized) version of a naturally secreted luciferase could also provide the combined benefits of high signal strength and rapid response rates, the inventors cloned the Metridia luciferase coding sequence into various RapidReporter plasmids (GeneStream) using a PCR strategy that deleted the 17 amino acid N-terminal signal peptide and fused the remaining Metridia luciferase cDNA to N-terminal and C-terminal coding sequences that included sequences encoding protein destabilizing elements. The modified Metridia luciferase is not secreted when expressed in mammalian cells. The precise intracellular location of the modified luciferase enzyme is assumed to be cytoplasmic. In the experiments described below, mammalian cells transfected with plasmids expressing either the native Metridia luciferase (hereafter referred to as "secreted Metridia luciferase") or the modified Metridia luciferase (hereafter referred to as "non-secreted Metridia luciferase") were lysed in the presence of a variety of lysis buffer compositions and bioluminescence measured.

Using the non-secreted Gaussia or Metridia luciferases with commercially available buffers, the bioluminescent signal strength was very low, particularly in samples in which luciferase activity was measured shortly after cell lysis. Only after some hours of incubation in lysis buffer did the modified luciferase gain high activity.

Without wishing to be bound by theory, it is suggested that the non-secreted Gaussia and Metridia luciferases adopt a less active conformation intracellularly but can adopt an active conformation following cell lysis, albeit slowly. The inventors then tested a variety of modifications to the lysis buffer components in an attempt to develop a formulation enabling shorter incubation periods and in which the luminescent signal comprises a stronger flash phase (higher sensitivity) and a more stable glow phase (rate of decay of the signal is reduced); in particular providing an environment promoting the conversion of the luciferase from an inactive conformation to an active conformation following cell lysis.

Part II

Benefits of Bromide Anion

Example 2

HeLa cells were transiently transfected with a plasmid expressing native, secreted Gaussia luciferase and 24 hrs later the conditioned medium was collected. Wells of a 96-well plate were loaded with 20 ul of conditioned medium and assayed for luciferase activity by injecting 60 ul of an assay buffer comprising 26 uM Cz; pH 8.1 plus the salt as indicated in FIG. 1. Results were expressed as a % of the light units obtained in the absence of salt (FIG. 1).

Light output with NaBr was higher than with either NaCl or no salt. It can be seen from FIG. 1 that NaBr enhances the activity of secreted Gaussia luciferase.

Example 3

HeLa cells stably expressing non-secreted and destabilized Gaussia luciferase were plated onto 96-well plates and incubated overnight. Medium was removed and the cells lysed in 30 ul of lysis buffer per well. The lysis buffer (LB) comprised; 25 mM Tris pH 7.8; 0.1% NP40; 1 mM EDTA plus NaBr at concentrations of (from left to right) 0 mM, 150 mM, 0 mM and 75 mM. Luciferase activity was assayed by injecting 30 ul of an assay buffer (AB) comprising 25 mM Tris pH 7.8; 40 uM Cz plus NaBr at concentrations of (from left to right) 0 mM, 0 mM, 150 mM and 75 mM. Thus, the final concentration of NaBr was 75 mM in all samples, except the no salt controls. Results were expressed as relative light units (RLU) (See FIG. 2).

Figure 2:
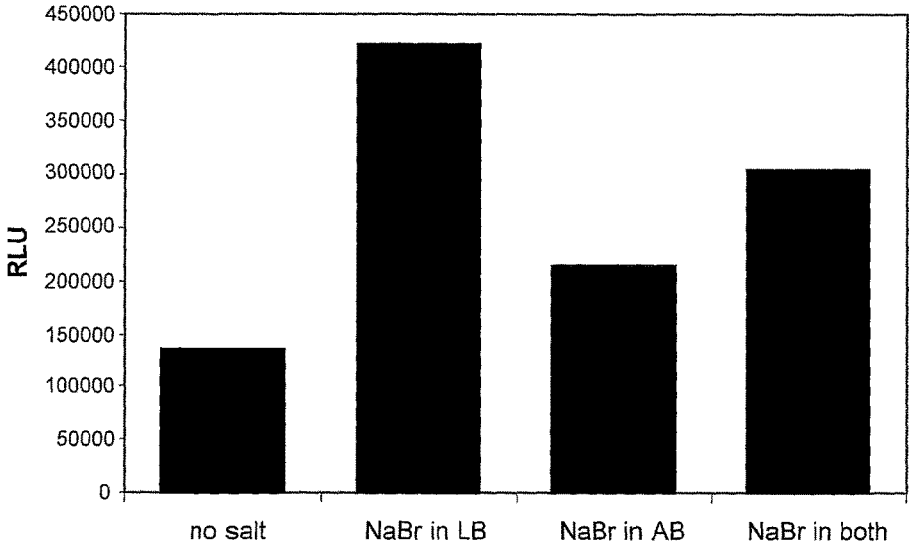
FIG. 2. shows the effect of NaBr on the activity of non-secreted Gaussia luciferase expressed in HeLa cells. The effect NaBr in the lysis buffer is compared to having NaBr in the assay buffer.

The data in FIG. 2 show that the beneficial effect of NaBr with secreted Gaussia luciferase (FIG. 1) also applies to the non-secreted and destabilized Gaussia. Moreover, the data show that it is advantageous to include NaBr in the lysis buffer (LB) as opposed to the assay buffer (AB). It can be seen that NaBr enhances activity of non-secreted Gaussia luciferase, especially when included in lysis buffer.

Example 4

Figure 3:
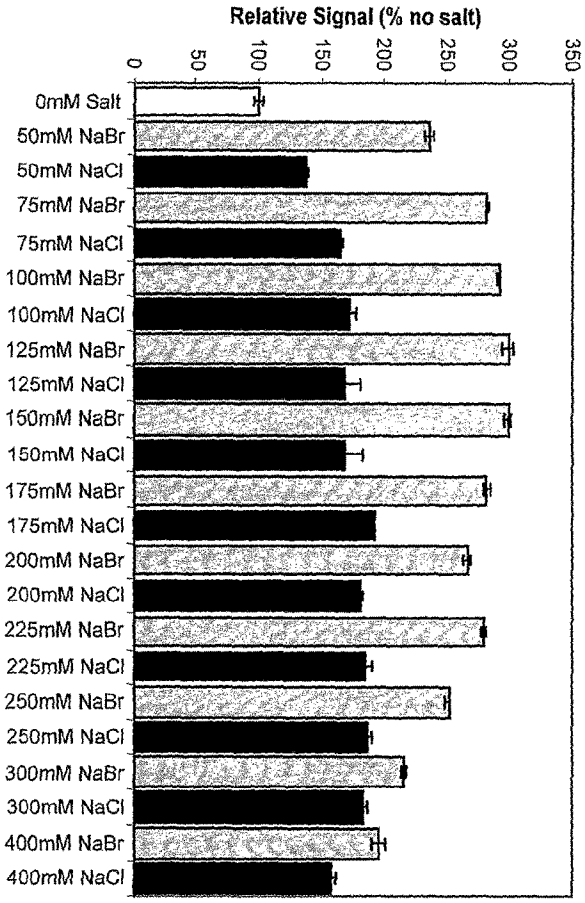
FIG. 3. shows the effect of bromide ions on non-secreted Gaussia luciferase activity fora range of concentrations of bromide ion.

HeLa cells stably expressing non-secreted and destabilized Gaussia luciferase were plated onto 96-well plates and incubated overnight. Medium was removed and the cells lysed in 20 ul of lysis buffer per well. The lysis buffer comprised; 25 mM Tris pH 8.1, 1 mM EDTA; 0.1% NP40; 63.4 uM Na-Oxalate; 5% Glycerol plus the concentration and type of salt indicated in FIG. 3. Luciferase activity was assayed at 40 min after addition of the lysis buffer (by injecting 60 ul of an assay buffer comprising 25 mM Tris pH 8.1; 1 mM EDTA, 2 mM Ascorbate; 26 uM Cz. Results were expressed as a % of the light units obtained in the absence of salt (see FIG. 3).

Both salts increased light output compared to no salt. However NaBr provided a superior enhancement to NaCl and enhancement was found to have some concentration dependency.

Example 5

Figure 4:
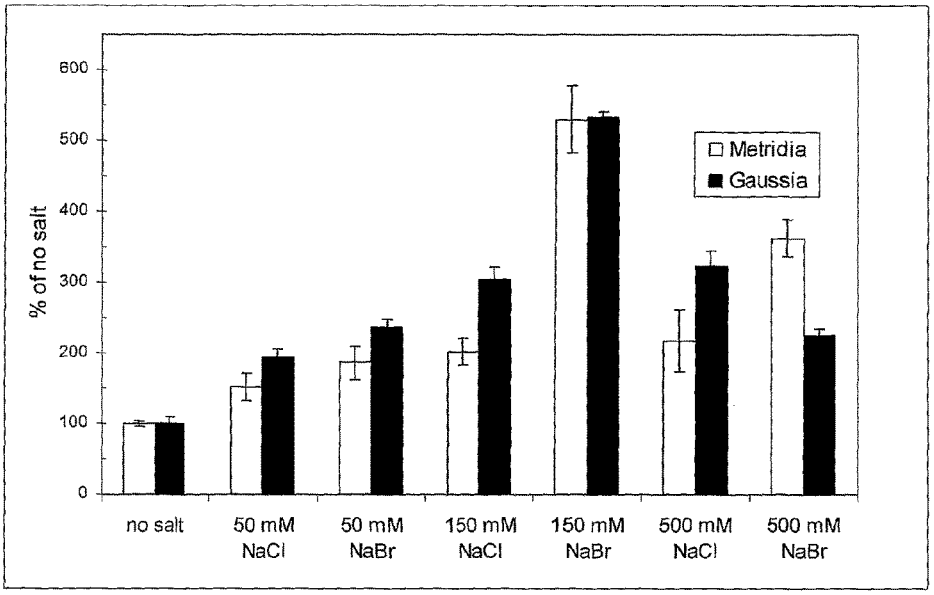
FIG. 4. shows the effect of bromide and chloride ions on non-secreted Metridia luciferase activity fora range of concentrations of bromide and chloride ion.

HeLa cells stably expressing either non-secreted and destabilized Gaussia or non-secreted and destabilized Metridia luciferase were plated onto 96-well plates and incubated overnight. Medium was removed and the cells lysed in 20 ul of lysis buffer per well. The lysis buffer comprised; 25 mM Tris pH 8.1; 0.1% NP40; 63.4 uM Na-Oxalate; 5% Glycerol plus the concentration and type of salt indicated in FIG. 4. Replicate samples were assayed for luciferase activity after 30 minutes following addition of the lysis buffer by injecting 60 ul of assay buffer. The assay buffer comprised 25 mM Tris pH 7.75; 2 mM Ascorbate; 24 uM Cz. Results were expressed as a % of the light units obtained in the absence of salt (see FIG. 4).

As was observed with non-secreted and destabilized Gaussia luciferase in Example 4, NaBr provided a superior enhancement to NaCl with non-secreted and destabilized Metridia luciferase. The enhancement was found to have some concentration dependency.

Example 6

Figure 5A:
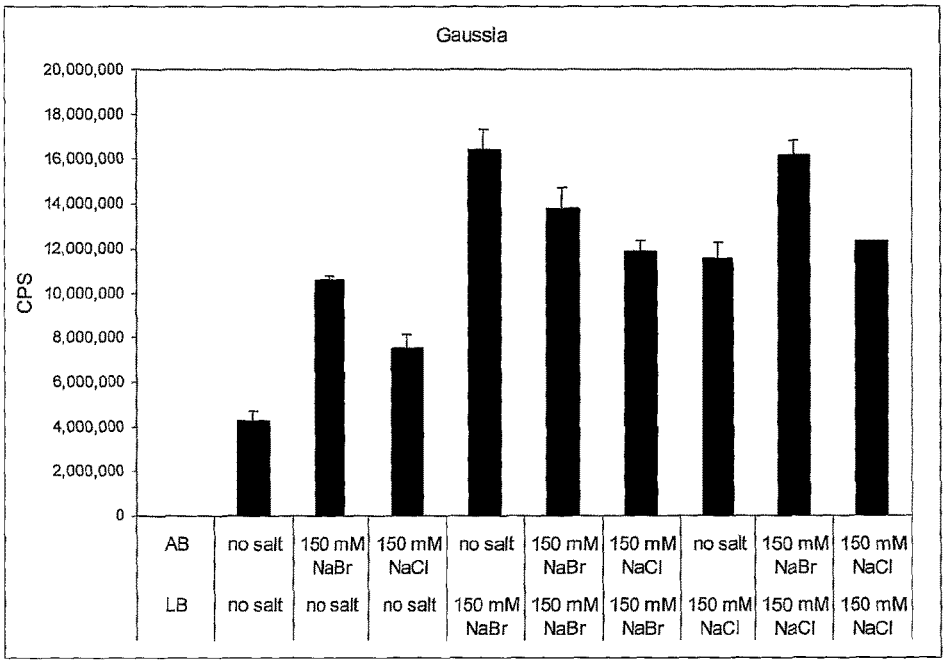
FIGS. 5A and 5B show a comparison of the effect of NaBr in the lysis buffer or assay buffer on the activity of non-secreted Gaussia luciferase and non-secreted Metridia luciferase expressed in HeLa cells.
Figure 5B:
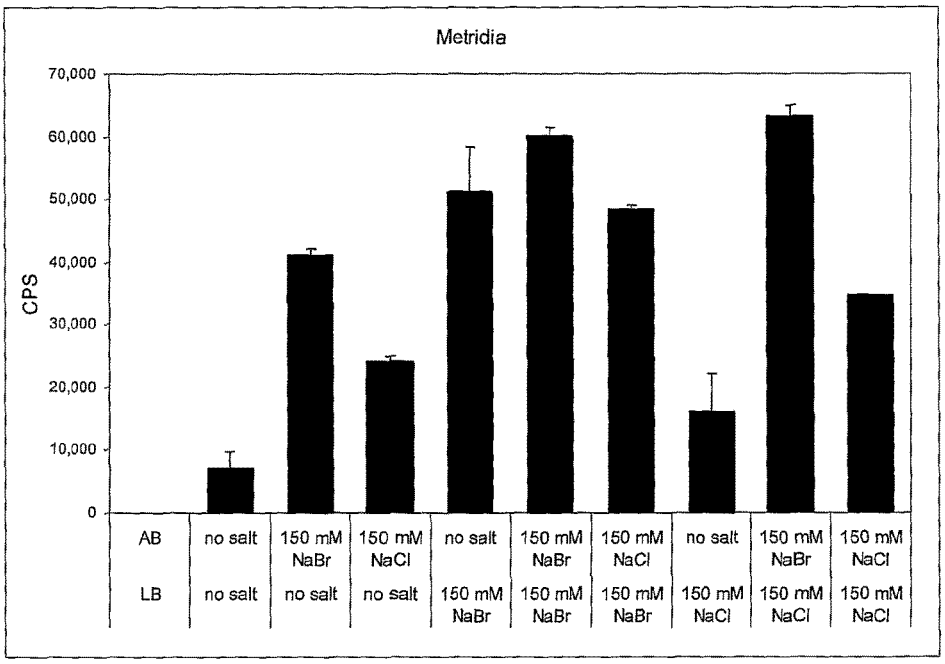

Luciferase assays were performed as described in Example 5 with either non-secreted and destabilized Gaussia luciferase or non-secreted and destabilized Metridia luciferase. Two experiments are shown as separate graphs, with results shown as relative luminescence in counts per second (CPS) (see FIGS. 5A and 5B). Within each experiment, the lysis buffer and assay buffer differed only in the amount and type of salt added as indicated. Replicate samples were analysed at 120 min after addition of the lysis buffer (LB) by injecting 60 ul of assay buffer (AB).

For both non-secreted Gaussia and non-secreted Metridia luciferase the signal strength is then lowest in the absence of salt. A higher signal strength was noted by including salt in either the lysis buffer or assay buffer. Furthermore, the bromide salt was superior to the chloride salt for both luciferases. Of the four treatment groups, the highest signal strength was seen when the bromide was included in the lysis buffer suggesting that in some circumstances it may be preferable to include the bromide in the lysis buffer rather than the assay buffer.

Example 7

Luciferase assays were performed as described in Example 4. All salts were present at 150 mM in lysis buffer.

Figure 6:
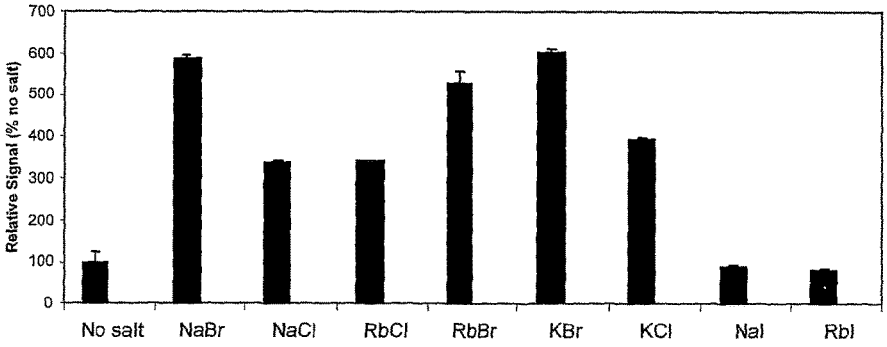
FIG. 6. shows the effect of anions compared to cations for enhancing non-secreted Gaussia luciferase activity with salt.

The highest level of signal enhancement (>5-fold) was achieved with NaBr, RbBr and KBr. A lower level of enhancement was seen with the corresponding Chloride salts and no enhancement was seen with iodide salts. These data demonstrate that, contrary to the existing literature, the anion and not the cation is important for achieving high luciferase activity. Moreover, they provide further evidence for the beneficial effect of bromide salts and demonstrate that a variety of different bromide salts can be used to achieve the desired effect (see FIG. 6).

Example 8

Figure 7:
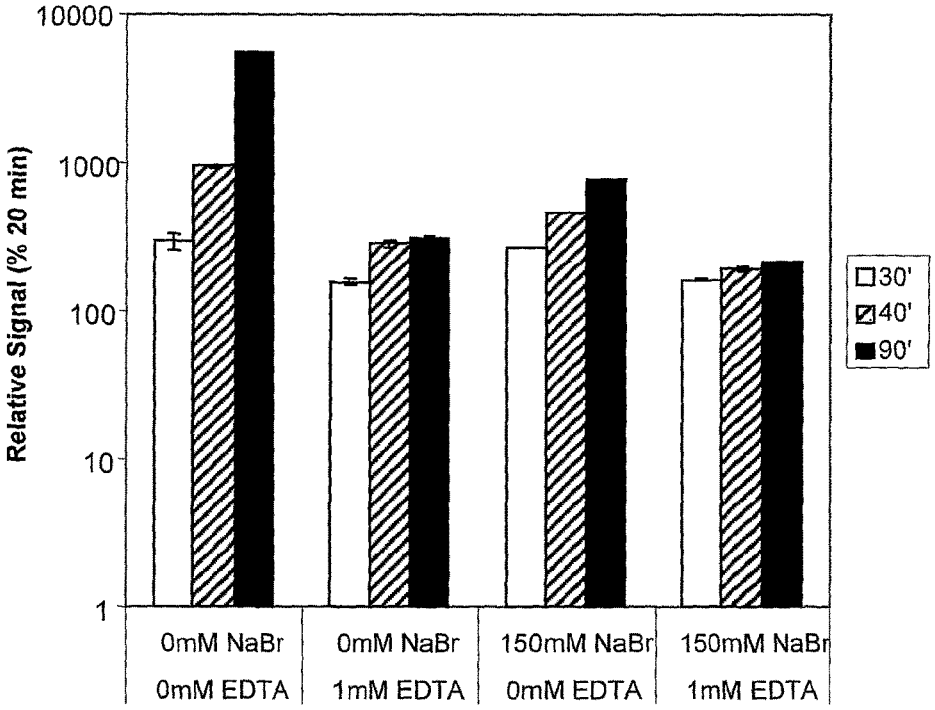
FIG. 7. shows the effect of NaBr with EDTA for reducing lysis times prior to measuring non-secreted Gaussia luciferase activity.

Luciferase assays were performed as described in Example 7, except using the indicated concentrations of salt and EDTA in the lysis buffer. Replicate samples were assayed for luciferase activity at 20, 30, 40 and 90 min after addition of lysis buffer. Results were expressed as a % of the light units obtained after 20 min lysis in the same lysis buffer (see FIG. 7).

In the absence of salt and EDTA, a dramatic increase in luciferase activity was evident between 20 and 90 min after the onset of cell lysis. A far more stable (and therefore more desirable) level of luciferase activity was achieved by addition of either EDTA or NaBr alone. However, an additive beneficial effect was achieved by combining both components into the lysis buffer. It can be seen that addition of NaBr and EDTA enables the use of reduced lysis times.

Part III

Benefit of Chelators

Example 9

Figure 8A:
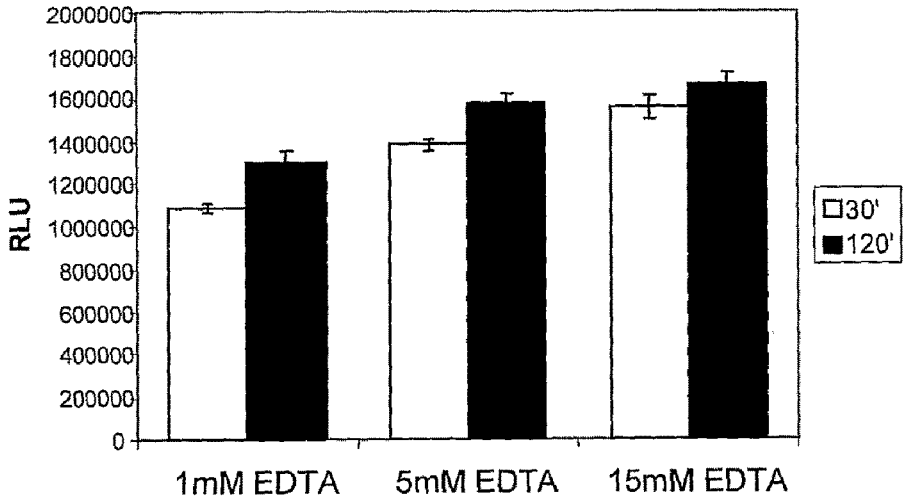
FIGS. 8A and 8B show the effect of EDTA across a range of concentrations as a chelator on non-secreted Gaussia luciferase activity.
Figure 8B:
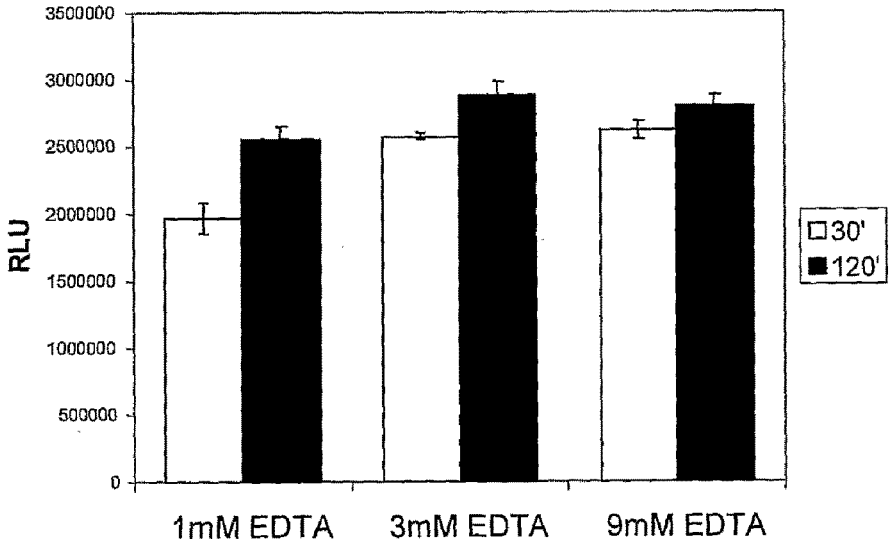

Luciferase assays were performed as described in Example 8, except using lysis buffer containing 150 mM NaBr and the indicated concentration of EDTA. Two experiments are shown as separate graphs, with results shown as relative light units (RLU) (see FIGS. 8A and 8B). Within each experiment, the same assay buffer was used for all samples and the lysis buffer differed only in the amount of EDTA as indicated. Replicate samples were assayed for activity of non-secreted Gaussia luciferase at 30 or 120 min after addition of lysis buffer. The benefit of 1 mM EDTA vs. no EDTA is shown in the previous graph. This graph demonstrates the benefit of higher amounts of EDTA in terms of both signal intensity and the stability of the luciferase signal over time in lysis buffer.

Example 10

Figure 9:
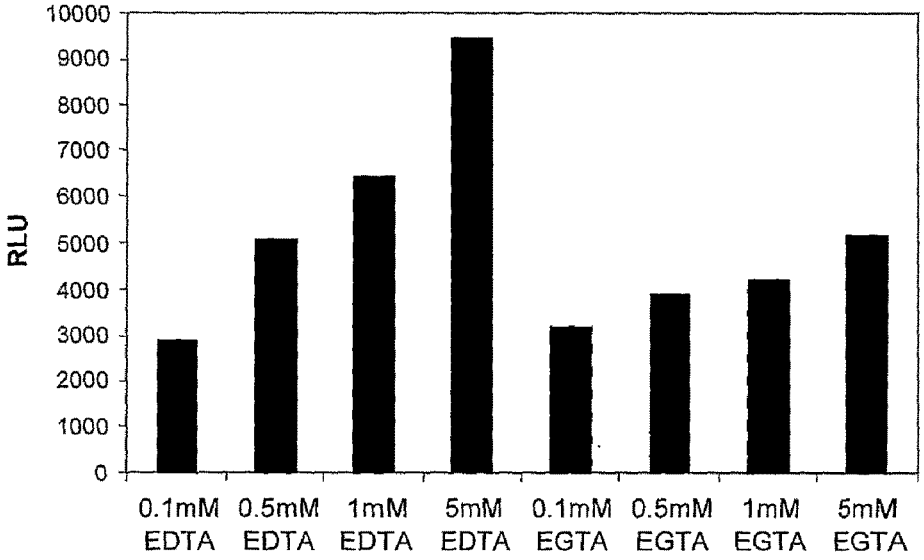
FIG. 9. shows a comparison of the effect of EDTA and EGTA as chelators on non-secreted Gaussia luciferase activity.

Luciferase assays were performed as described in Example 9, except using the indicated type and concentration of chelator and a 30 min lysis period. The results show that both EDTA and EGTA provide a concentration-dependent beneficial effect on signal intensity (see FIG. 9).

Example 11

Figure 10A:
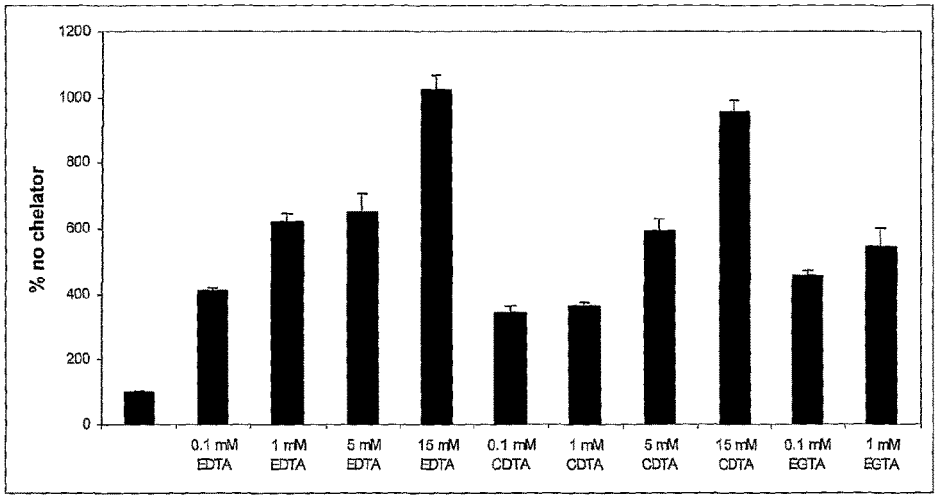
FIGS. 10A and 10B show a comparison of the effect of EDTA, CDTA and EGTA as chelators on non-secreted Metridia luciferase activity.
Figure 10B:
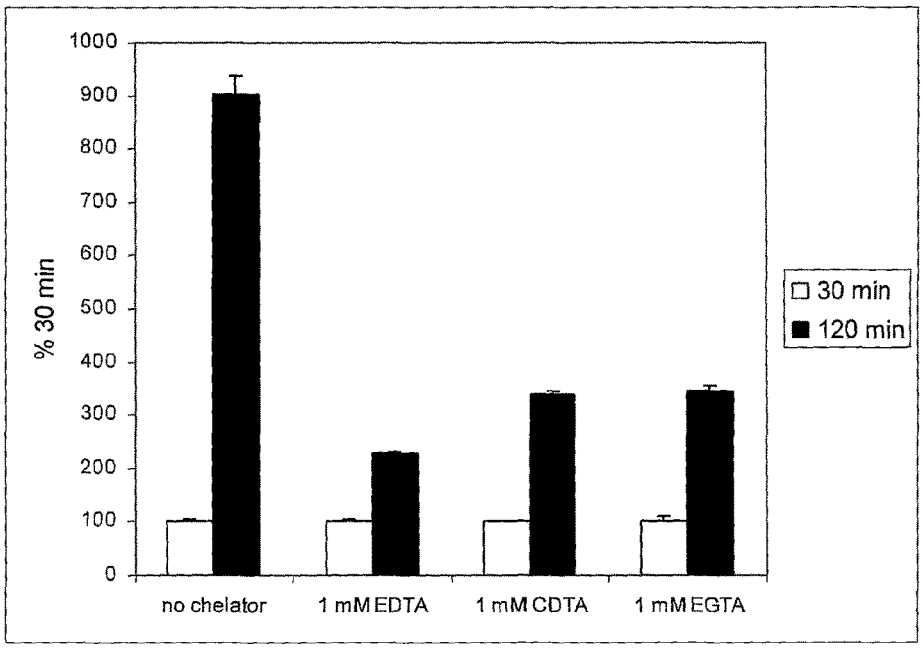

Luciferase assays were performed with non-secreted and destabilized Metridia luciferase as described in Example 5, except the lysis buffer contained no salt and but contained the indicated type and concentration of chelators. Replicate luciferase assay were carried out after a 30 or 120 min lysis period. Results from the 30 min time point were expressed as a % of the light units obtained in the absence of chelator (see FIG. 10A) and results from the 120 min time point were expressed as % of the light units obtained with the same lysis buffer at 30 min (see FIG. 10B). The results show that EDTA, CDTA and EGTA provide a concentration-dependent beneficial effect on signal intensity and additionally reduce the effect if lysis time.

Example 12

Figure 11A:
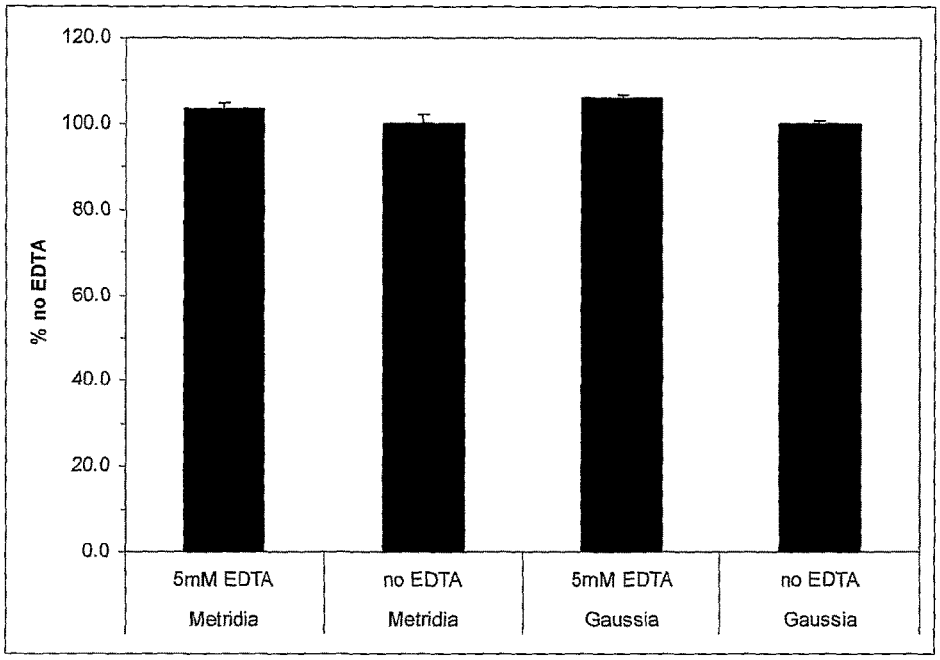
FIGS. 11A and 11B show the effect of EDTA as a chelator across a range of concentrations on secreted Gaussia luciferase and secreted Metridia luciferase activity.
Figure 11B:
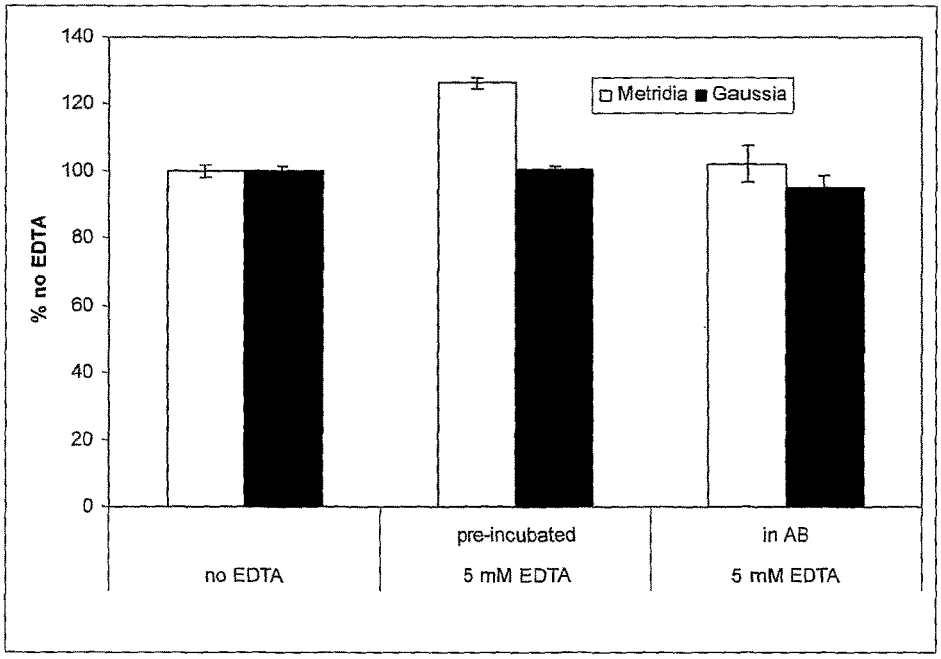

Flasks of HeLa cells transiently expressing secreted Gaussia or secreted Metridia luciferases were incubated overnight. Aliquots of conditioned media were removed and diluted 1:10 into fresh medium (RPMI+10% fetal calf serum) with or without 5 mM EDTA. After 30 min, 80 ul aliquots were assayed for luciferase activity by injecting 20 ul medium containing 48 uM Cz. Results were expressed as the % of the light units obtained in the absence of EDTA (see FIG. 11A). A second experiment was performed in the same manner except that the incubation time was increased to 90 min and some samples received assay buffer that additionally contained 5 mM EDTA (see FIG. 11B).

The data show that the benefits of addition of chelators noted with non-secreted Gaussia and non-secreted Metridia luciferase (see Examples 9, 10 and 11) do not apply to the (native) secreted versions of the same luciferases. In particular, there is a lack of any enhancement in samples that received the chelator only in the assay buffer (see FIG. 11B). This suggests that the effect of the chelator does not occur at the level of the substrate nor at the moment of initiation of the reaction. Rather, it appears that the benefit of chelator occurs at the level of the luciferase protein prior to the enzymatic reaction, for example, by the chelator assisting the luciferase protein in adopting a more active format.

When expressed intracellularly, it has been shown that the secreted luciferases adopt a less active format such that the positive effect of chelator is pronounced with the intracellular versions that require refolding or other modifications in order to adopt the high activity state of the protein. This beneficial effect of chelator on luciferase activity has not previously been described.

Example 13

Figure 12:
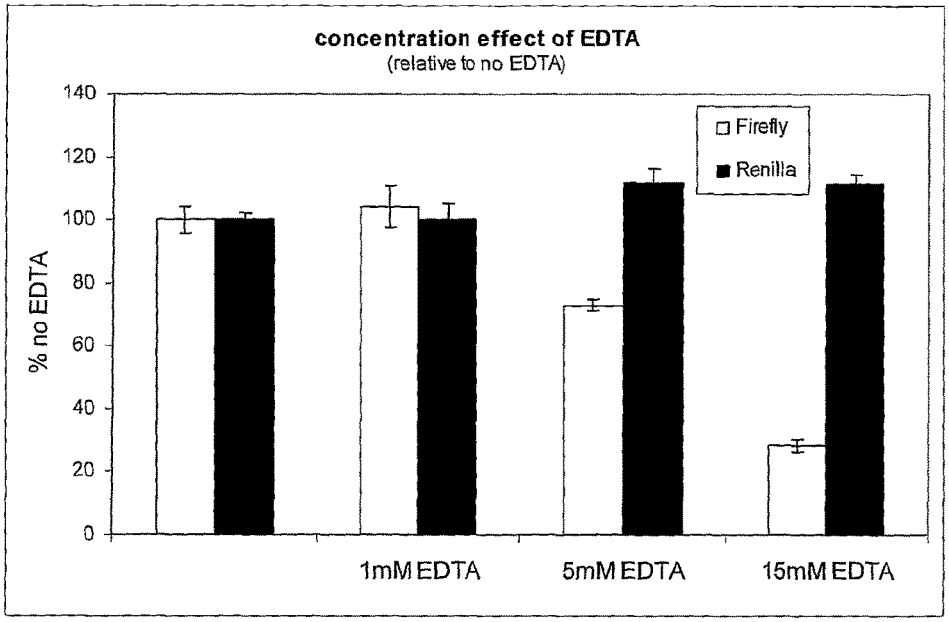
FIG. 12. shows the effect of EDTA across a range of concentrations on Firefly and Renilla luciferases.

HeLa cells expressing Firefly or Renilla luciferases were plated into 96-well plates and incubated overnight. Medium was removed and the cells lysed in 20 ul of lysis buffer containing 25 mM Tris pH 8.1; 0.1% NP40; 63.4 uM Na-Oxalate; 5% Glycerol, 150 mM NaCl plus the concentration of EDTA in FIG. 12. Replicate samples were assayed for luciferase activity at 30 min by injecting 30 ul of Firefly assay buffer II containing Firefly substrate followed by 30 ul of Promega's "Stop and Glo" buffer containing Renilla substrate. Results are expressed as a % of the light units obtained in the absence of EDTA (see FIG. 12).

The results indicate that the addition of EDTA to Renilla and firefly luciferases does not provide the same beneficial effect on signal intensity as is observed with non-secreted Gaussia or Metridia luciferases. In fact, the addition of EDTA clearly decreases the activity of Firefly luciferase.

Part IV

Type and Concentration of Detergent

Example 14

Figure 13A:
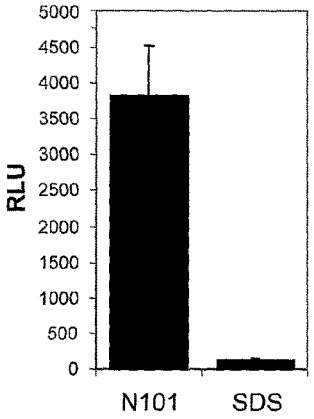
FIGS. 13A, 13B and 13C show the effect of various detergents on non-secreted Gaussia luciferase activity.
Figure 13B:
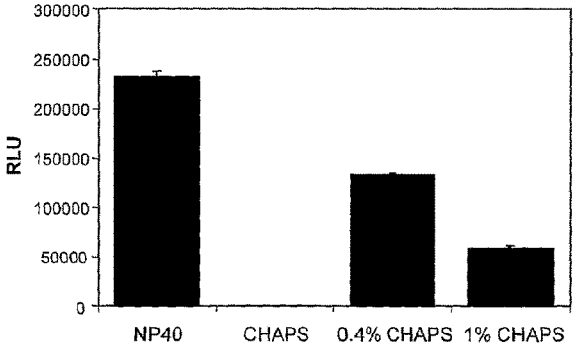
Figure 13C:
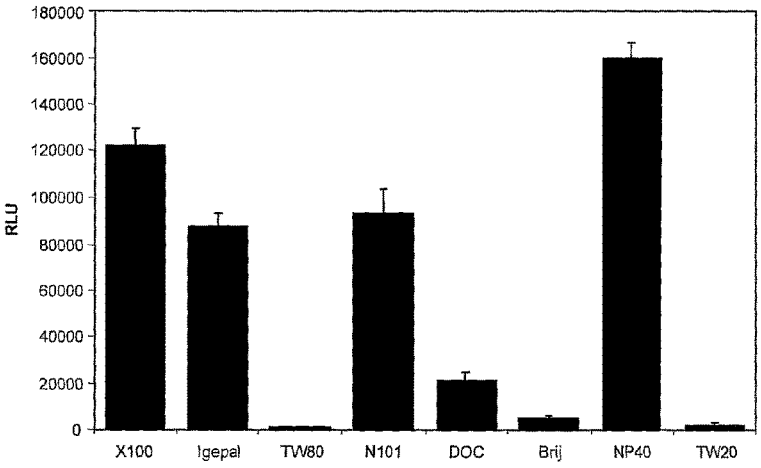

HeLa cells expressing destabilised, non-secreted Gaussia luciferase were plated in equal aliquots onto 96-well plates and incubated overnight. Three experiments are shown as separate graphs (FIGS. 13A, 13B and 13C). Within each experiment, the same assay buffer was used for all samples and the lysis buffer differed only in the type of detergent used (0.1% in lysis buffer unless otherwise indicated). The anionic detergents, SDS and DOC do not perform well with Gaussia luciferase, presumably because they inhibit luciferase activity. The Zwitterionic detergent, CHAPS, appeared not to lyse the cells at 0.1% and the same is probably true for the non-ionic detergents, Tween 20, Tween 80 and Brij. The remaining detergents, which are all non-ionic performed well, with NP40 providing the highest signal intensity.

Example 15

Figure 14A:
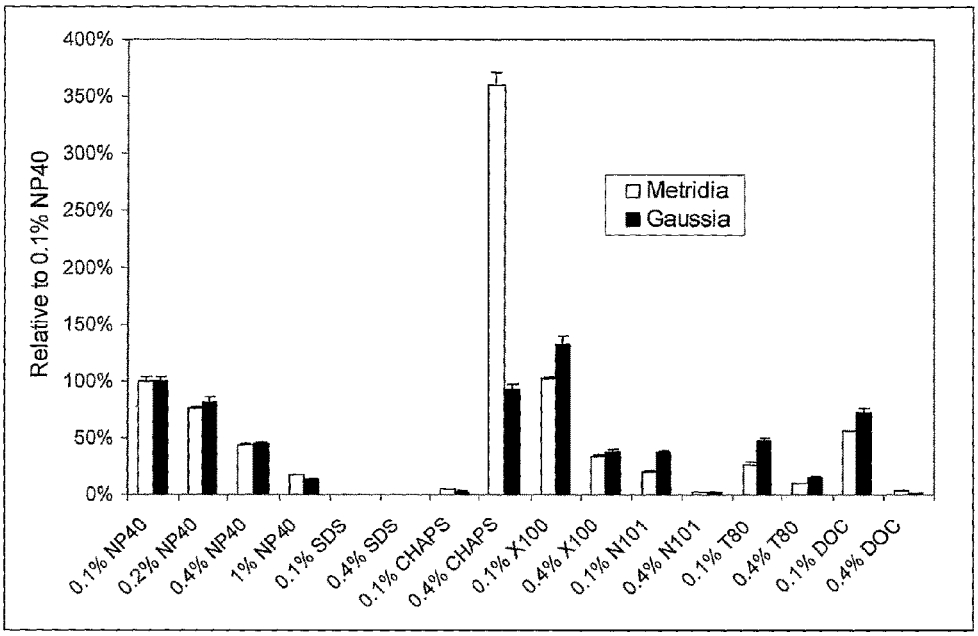
FIGS. 14A and 14B show the effect of various detergents on non-secreted Gaussia luciferase and non-secreted Metridia luciferase activity

HeLa cells expressing destabilised, non-secreted Gaussia or non-secreted Metridia luciferases were plated in equal aliquots onto 96-well plates and incubated overnight. Medium was removed and the cells lysed in 20 ul of lysis buffer. The detergent type and concentration was varied as indicated. Luciferase assays were carried out by injecting 60 ul of assay buffer comprising 25 mM Tris pH 8.1; 1 mM EDTA, 2 mM Ascorbate; 24 uM Cz Two experiments are shown, in the first the lysis buffer also contained 5% glycerol, 64 uM sodium oxalate, 150 mM NaBr, 25 mM Tris pH 8.5, 5 mM EDTA, 0.6 mM reduced glutathione, 0.4 mM oxidised glutathione, 75 mM urea (v6) and luciferase activity was assayed at 40 min. In the second experiment, the lysis buffer also contained 2 5 mM Tris pH 8.1, 63.4 uM Na-oxalate, 150 mM NaBr, 5% Glycerol and the luciferase activity was assayed at 120 min. Results were expressed as the % of the light units obtained using 0.1% NP40 (see FIGS. 14A and 14B).

Figure 14B:
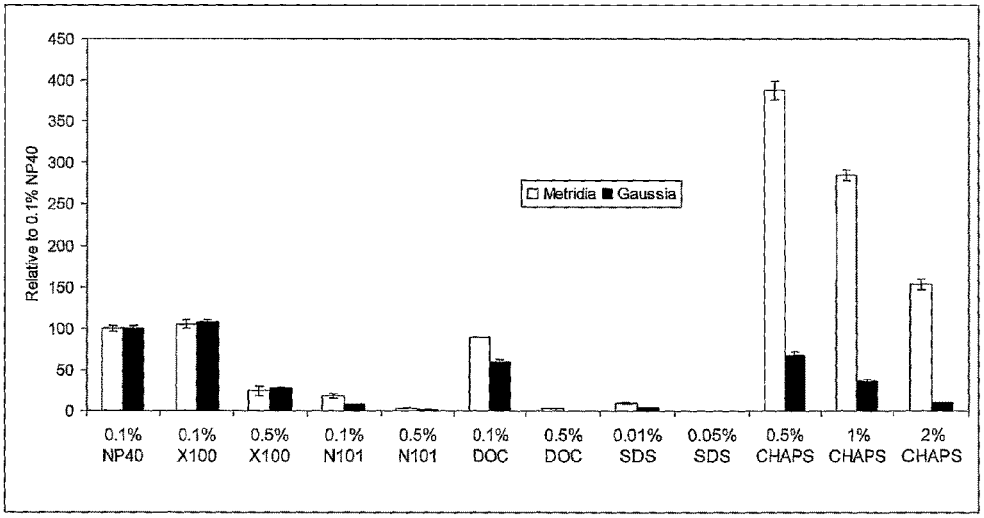

The results from the first experiment (see FIG. 14A) indicated that 0.1% SDS blocks enzymatic activity and that 0.1% CHAPS is insufficient to lyse the cells, therefore different concentration ranges of these detergents were used in the second experiment (see FIG. 14B).

The results show that the detergents provide a concentration-dependent inhibition on signal intensity. This effect was most evident with the anionic detergents SDS and DOC. CHAPS, a zwitterionic detergent, provided the highest activity for non-secreted Metridia luciferase, notably, this detergent required a higher concentration to effectively lyse the cells. The remaining detergents, which are all non-ionic, performed well, with NP40 and Triton X100 providing the highest signal intensity.

Experiments with the cationic detergent CTAB (not shown) indicate that as with anionic detergent cationic detergents have a strong inhibitory effect on signal intensity.

Example 16

Figure 15A:
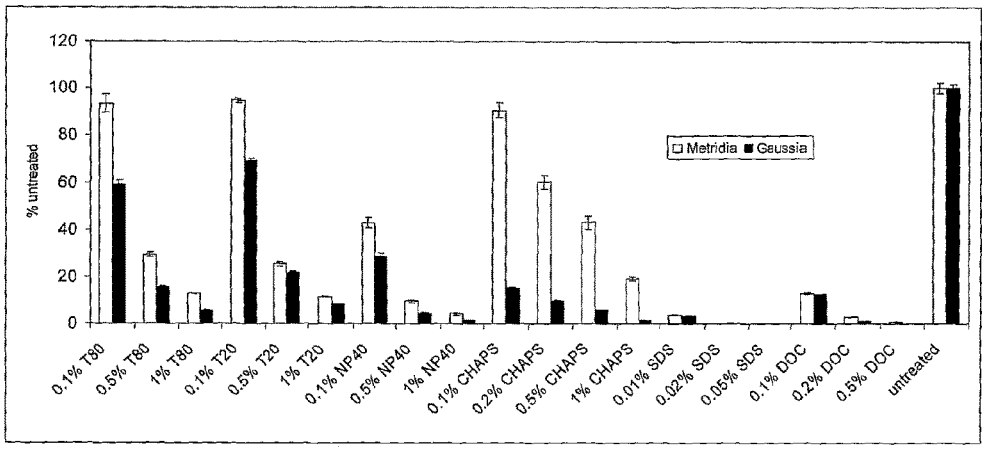
FIGS. 15A and 15B show the effect of various detergents on secreted Gaussia luciferase activity and secreted Metridia luciferase activity.
Figure 15B:
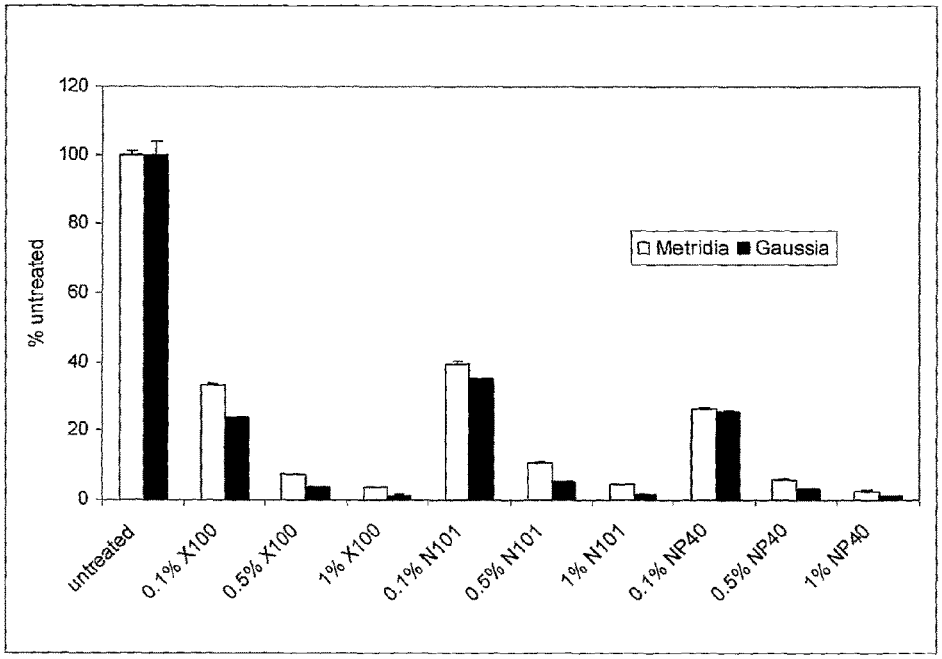

HeLa cells expressing secreted Gaussia or secreted Metridia luciferase were plated in equal aliquots onto 96-well plates and incubated overnight. Medium was removed and diluted 1:10 into fresh medium containing the type and concentration of detergent indicated in FIGS. 15A and 15B. After 30 min, 80 ul were removed, 20 ul of medium containing 48 uM Cz added and the samples assayed for luciferase (see FIGS. 15A and 15B) Results were expressed as the % of the light units obtained in the absence of detergent.

The results from both experiments indicate that, as with non-secreted Gaussia and non-secreted Metridia luciferases there is a concentration-dependent inhibitory effect of these detergents on the signal intensity derived from the secreted forms of these luciferases.

Example 17

Figure 16A:
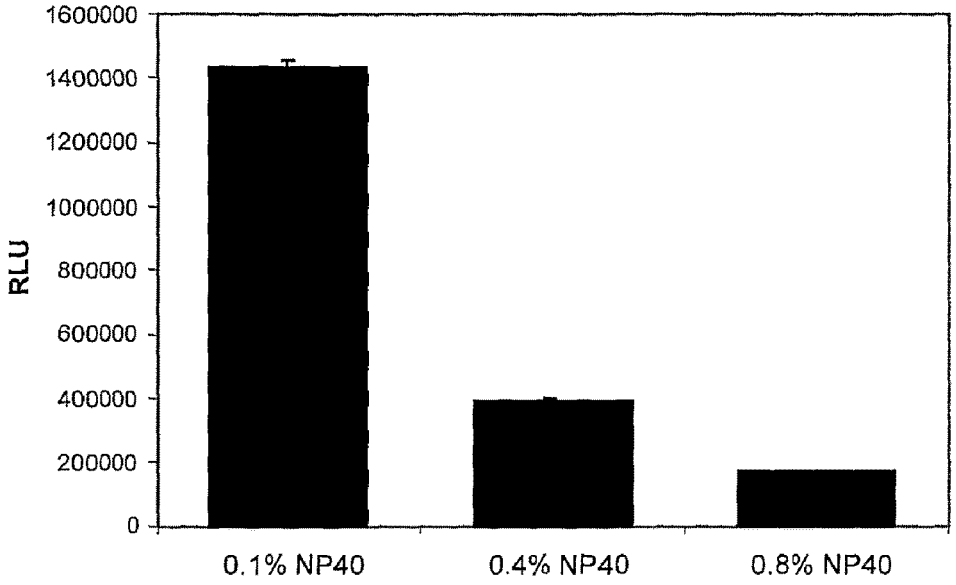
FIGS. 16A and 16B show the effect of detergent concentration on non-secreted Gaussia luciferase activity.
Figure 16B:
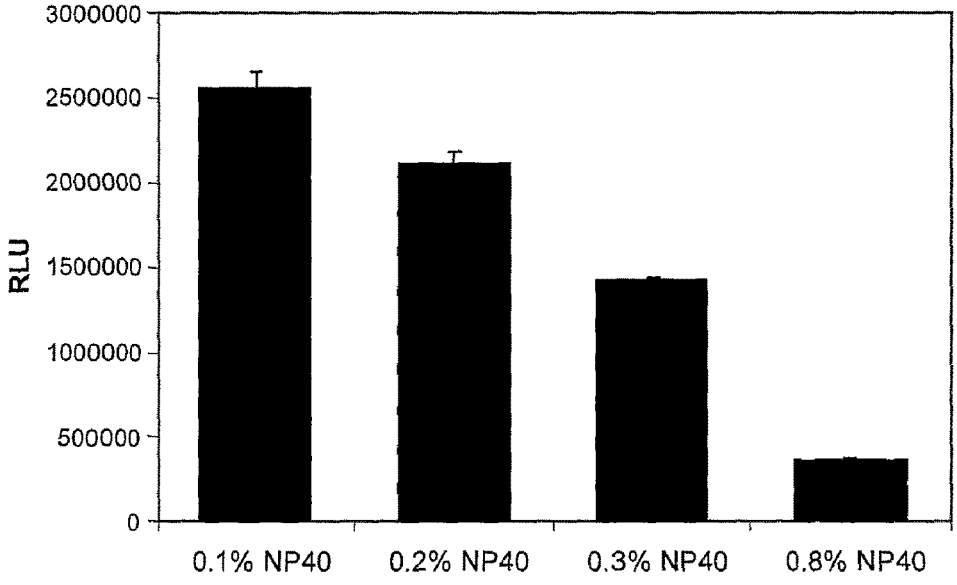

HeLa cells expressing destabilised, non-secreted Gaussia luciferase were plated in equal aliquots onto 96-well plates and incubated overnight. Two experiments are shown as separate graphs (see FIGS. 16A and 16B). Within each experiment, the same assay buffer was used for all samples and the lysis buffer differed only in the % NP40. The highest signal was seen with 0.1% and signal strength declined with increasing amounts of detergent. It can be seen that luciferase activity is inhibited by detergent in a concentration-dependent manner.

Example 18

Figure 17:
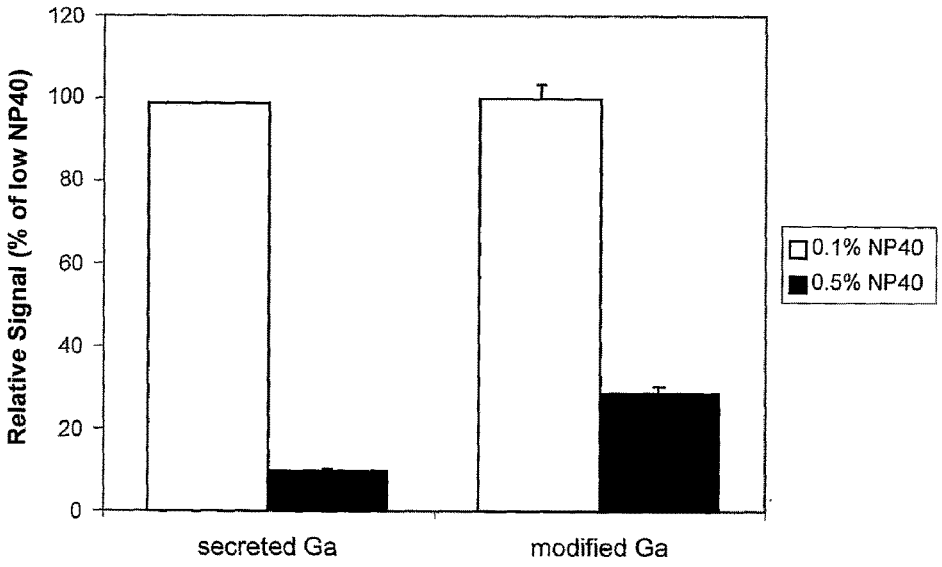
FIG. 17. shows the effect of detergent concentration on secreted and non-secreted Gaussia luciferase activity.
Figure 18A:
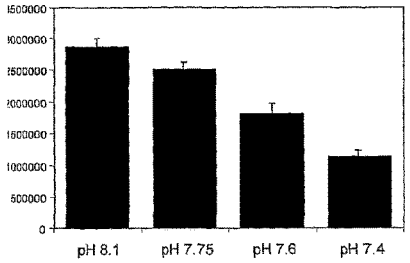
FIGS. 18A, 18B, 18C and 18D show the effect of higher pH on non-secreted Gaussia luciferase activity.
Figure 18B:
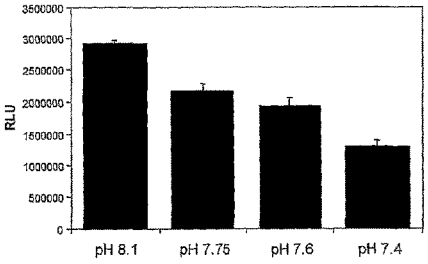
Figure 18C:
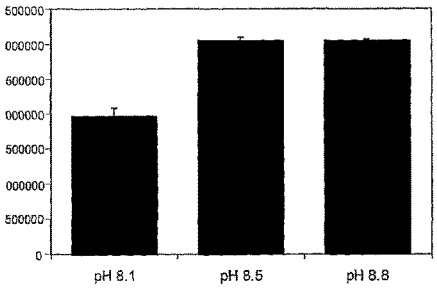
Figure 18D:
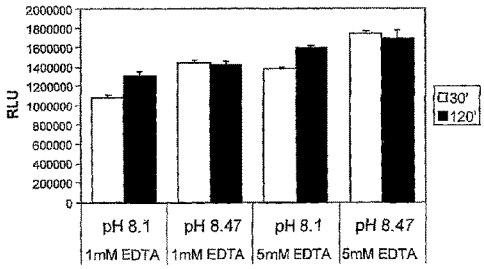

The effect of detergent concentration on the activity of non-secreted Gaussia luciferase was determined as described in Example 17, except the experiment was also performed with cells expressing the secreted Gaussia. For such cells, the conditioned medium was used as a source of the secreted Gaussia protein, to which the detergent was added in the indicated concentrations. The results demonstrate that inhibition of luciferase activity by detergent occurs with both secreted and non-secreted Gaussia luciferase (see FIG. 17).

Part V pH

Example 19

Luciferase assays were performed as described in Example 9, except using lysis buffer with the indicated pH. EDTA was present at 1 mM except where indicated. Four experiments are shown as separate graphs (see FIGS. 18A, 18B, 18C and 18D). Lysis times were 40 minutes for A and B, 30 minutes for C; and in D, and replicate samples were assayed for Gaussia luciferase activity at 30 or 120 minutes after addition of lysis buffer. These data demonstrate the benefit of higher pH in terms of both signal intensity and the stability of the luciferase signal over time in lysis buffer. The combination of high pH and high EDTA was particularly effective.

Example 20

Figure 19:
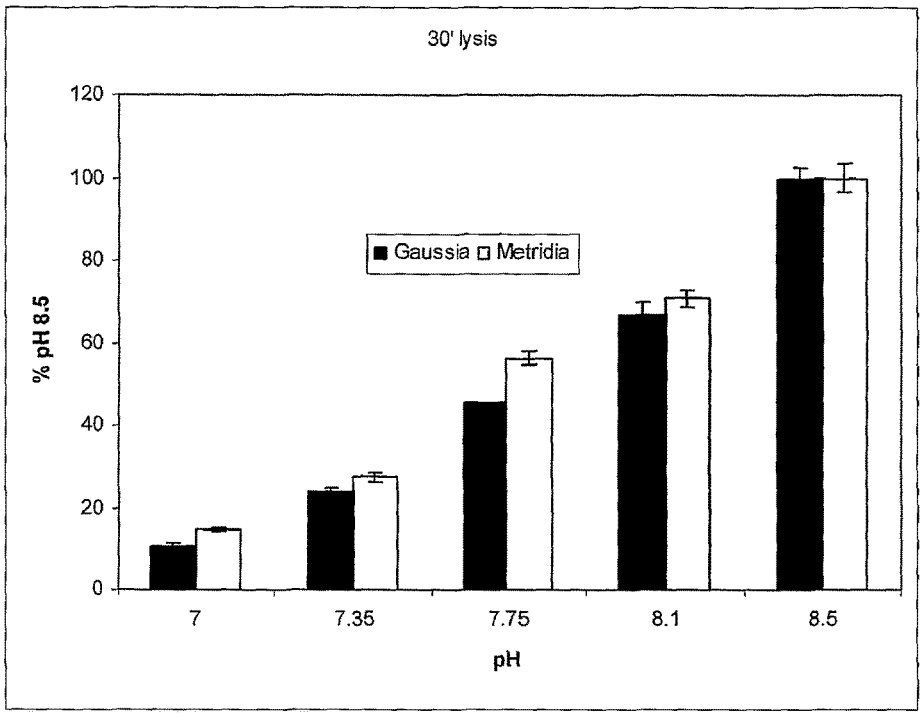
FIG. 19. shows the effect of pH on non-secreted Gaussia luciferase and non-secreted Metridia luciferase activity.

HeLa cells expressing destabilised, non-secreted Gaussia or non-secreted Metridia luciferases were plated in equal aliquots onto 96-well plates and incubated overnight. Medium was removed and the cells lysed in 20 ul of lysis buffer. The lysis buffer comprised 63.4 uM Na-oxalate, 5% Glycerol, 150 mM NaBr and 25 mM Tris at the indicated pH. Luciferase assays were carried out at 30 min by injecting 60 ul of assay buffer comprising 25 mM Tris pH 7.75; 2 mM Ascorbate; 24 uM Cz. Results were expressed as the % of the light units obtained at pH 8.5 (see FIG. 19).

The data demonstrates that the benefit of a lysis buffer with a higher pH, in terms of both signal intensity and the stability of the luciferase signal over time, is observed with both non-secreted Gaussia and Metridia luciferase. By contrast, in similar experiments conducted using firefly and Renilla luciferases suggest that there is no beneficial effect of high pH during cell lysis for these naturally intracellular luciferases (data not shown).

Part VI

Oxidising Agent

Example 21

Figure 20:
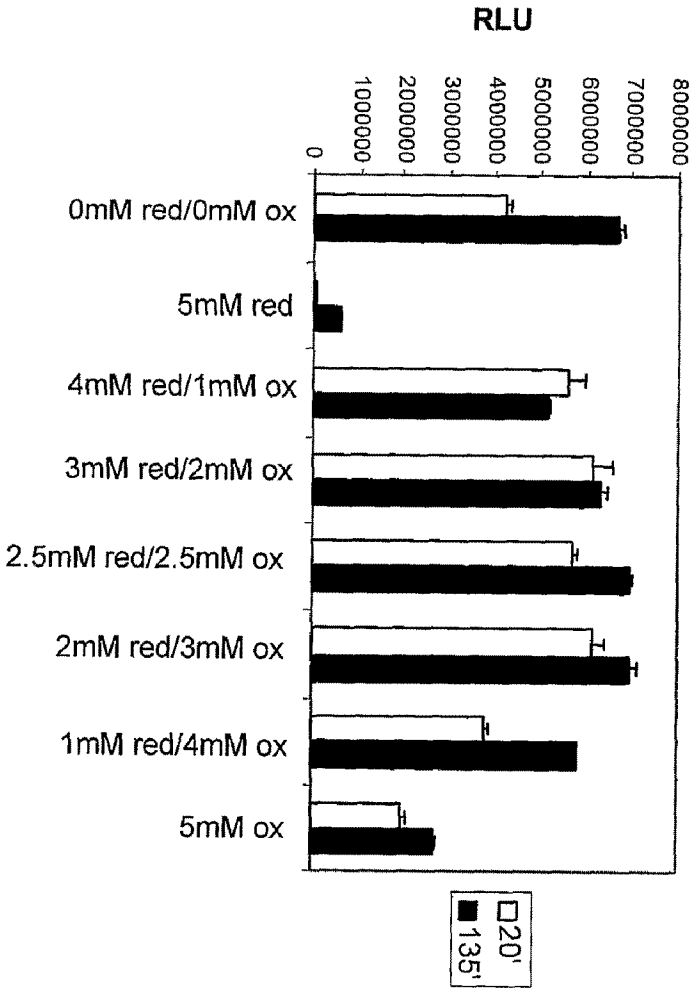
FIG. 20. shows the effect of oxidising agents at various concentrations and ratios on non-secreted Gaussia luciferase activity.

Luciferase assays were performed as described in Example 18, with EDTA at 5 mM and pH 8.5. The lysis buffer also contained the indicated concentrations of reduced (red) and oxidised (ox) glutathione. Replicate samples were assayed for Gaussia luciferase activity at 20 or 135 minutes after addition of lysis buffer. These data demonstrate that the presence within the lysis buffer of oxidised glutathione, and more preferably a mixture of reduced and oxidised glutathione, increases the rate at which the luciferase acquires its maximum activity during the cell lysis step (see FIG. 20).

Example 22

Figure 21:
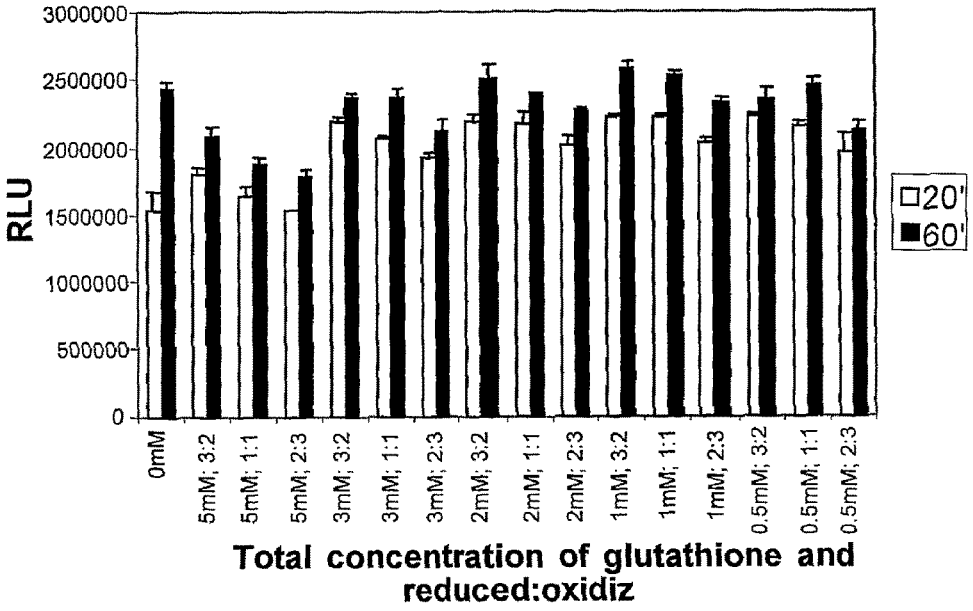
FIG. 21. shows the effect of oxidising agents at various concentrations and ratios on non-secreted Gaussia luciferase activity.

Luciferase assays were performed as described in Example 21, using the indicated total amounts of glutathione and ratio of reduced:oxidized. Replicate samples were assayed for Gaussia activity at 20 or 60 minutes after addition of lysis buffer. These data demonstrate that at all concentrations and ratios tested, the presence of glutathione in lysis buffer increases the rate at which the luciferase acquires its maximum activity during the cell lysis step. At the higher concentrations of reduced glutathione, a somewhat reduced signal was seen at 60 minutes (see FIG. 21).

Example 23

Figure 22:
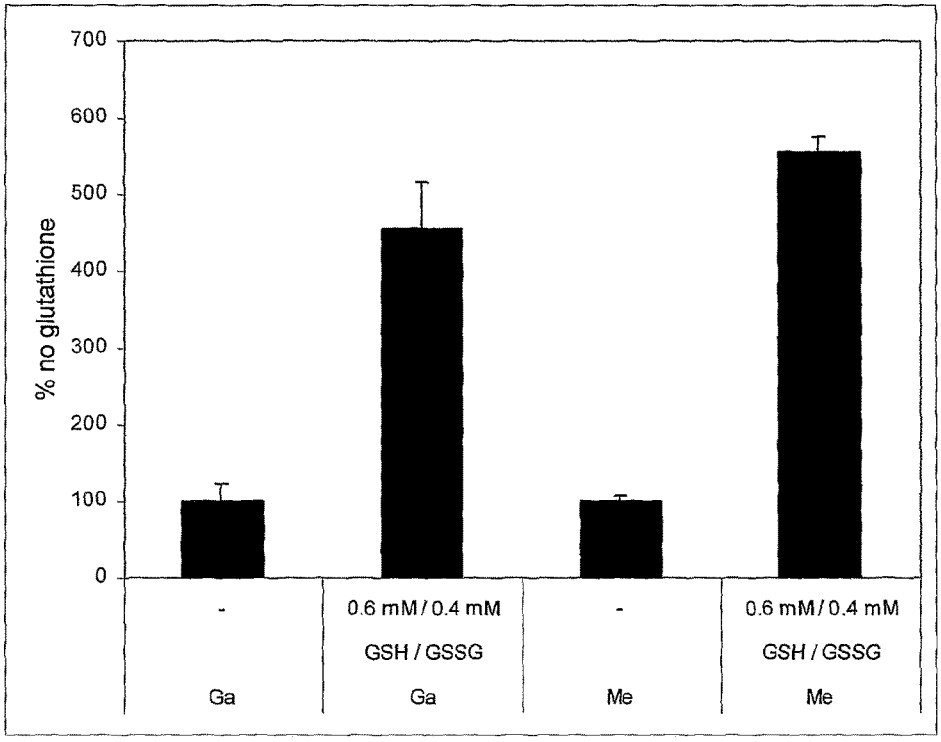
FIG. 22. shows a comparison of the effect of oxidising agents on non-secreted Gaussia luciferase and non-secreted Metridia luciferase activity.

HeLa cells transiently expressing either non-secreted Gaussia luciferase or non-secreted Metridia luciferase were plated onto 96-well plates and incubated overnight. Medium was removed and the cells lysed in 20 ul of lysis buffer per well, comprising 25 mM Tris pH 8.1, 63.4 uM Na-oxalate, 0.1% NP40, 5% Glycerol and either no glutathione or a combination of 0.6 mM reduced glutathione and 0.4 mM oxidised glutathione. Replicate samples were assayed for luciferase activity at 30 min after addition of lysis buffer by injecting 60 ul of an assay buffer comprising 25 mM Tris pH 7.75, 0.6 mM reduced glutathione, 0.4 mM oxidised glutathione, 1 mM EDTA, 2 mM Ascorbate, 24 uM Cz Results were expressed as the % of the light units obtained in the absence of glutathione for the same luciferase (see FIG. 22).

The data demonstrates that at the ratio tested, the presence of glutathione in the lysis and assay buffer also increases the signal of both non-secreted Gaussia and non-secreted Metridia luciferases.

Example 24

Figure 23A:
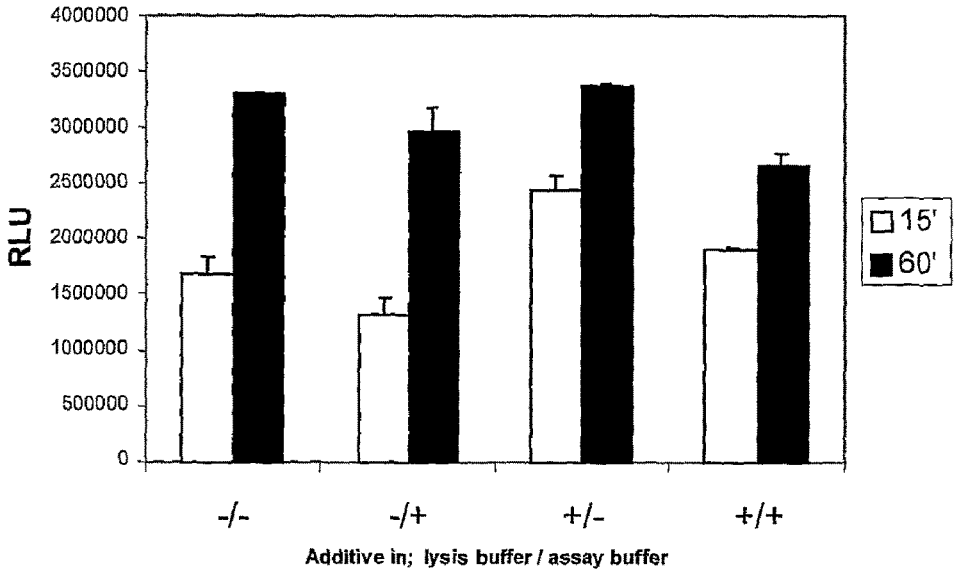
FIGS. 23A and 23B show the effect of oxidising agents in either lysis buffer and/or assay buffer on non-secreted Gaussia luciferase activity.
Figure 23B:
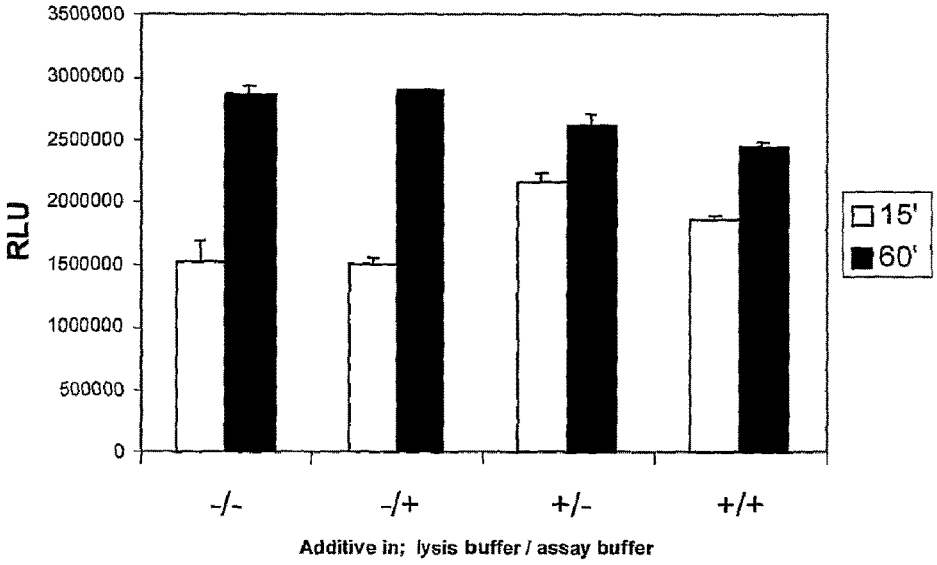

Luciferase assays were performed as described in Example 22 except using a single concentration and ratio of additive (glutathione; 1.2 mM reduced, 0.8 mM oxidised) in either the lysis buffer and/or assay buffer or neither. Two experiments are shown as separate graphs (see FIGS. 23A and 23B). Replicate samples were assayed for Gaussia luciferase activity at 15 or 60 minutes after addition of lysis buffer. These data demonstrate that the presence of glutathione in lysis buffer but not assay buffer increases the signal attained after a short (15 min) lysis period.

Example 25

Figure 24:
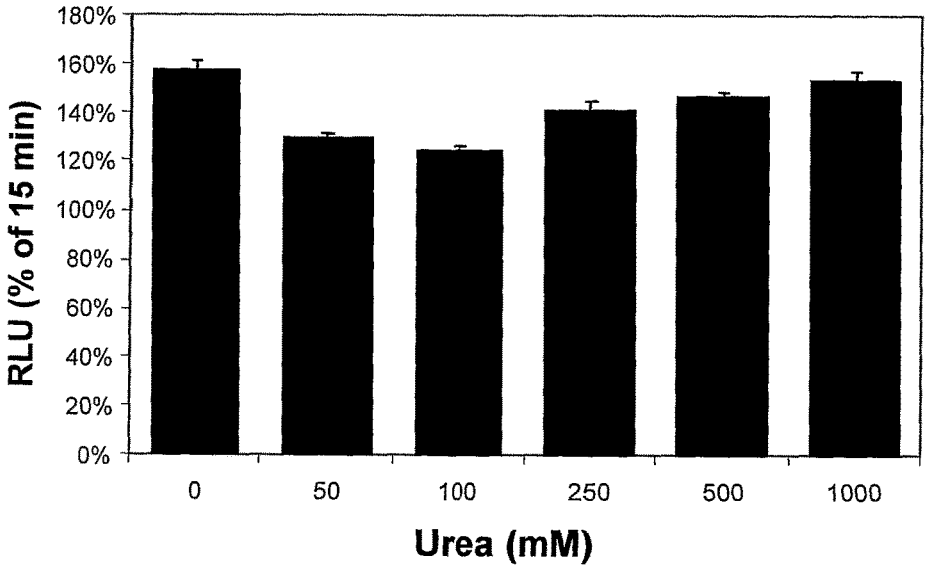
FIG. 24. shows the effect of urea at various concentrations on non-secreted Gaussia luciferase activity.

Luciferase assays were performed as described in Example 23 with the glutathione in both lysis buffer and assay buffer. Additionally, the lysis buffer contained the indicated concentrations of urea. Replicate samples were assayed for Gaussia luciferase activity at 15 or 60 minutes after addition of lysis buffer and the 60 min data were expressed as a % of the signal at 15 mins. All lysis buffers showed an increase in signal during this time. However, the increase was less pronounced with 50-100 mM urea suggesting that maximum activity can be reached sooner under these conditions (see FIG. 24).

Example 26

Figure 25:
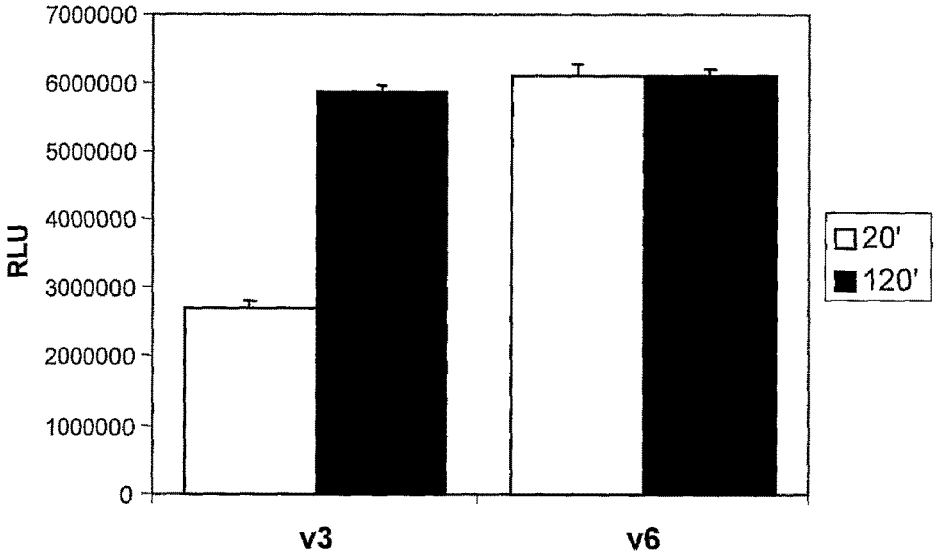
FIG. 25. shows the effect of combining NaBr, chelating agent, detergent and oxidising agent on non-secreted Gaussia luciferase activity.

HeLa cells expressing destabilised, non-secreted Gaussia luciferase were plated in equal aliquots onto 96-well plates and incubated overnight. The same assay buffer was used for all samples. Replicate samples were assayed for luciferase activity at 20 or 120 minutes after addition of lysis buffer containing 5% glycerol, 64 uM sodium oxalate, 0.1% NP40, 150 mM NaBr plus either 25 mM Tris pH 8.1, 1 mM EDTA (v3) or 25 mM Tris pH 8.5, 5 mM EDTA, 0.6 mM reduced glutathione, 0.4 mM oxidised glutathione, 75 mM urea (v6). Whereas v3 lysis buffer achieved only ~50% maximal activity after 20 mins lysis, the v6 lysis buffer achieved 100% activity within 20 mins (see FIG. 25).

Example 27

Figure 26:
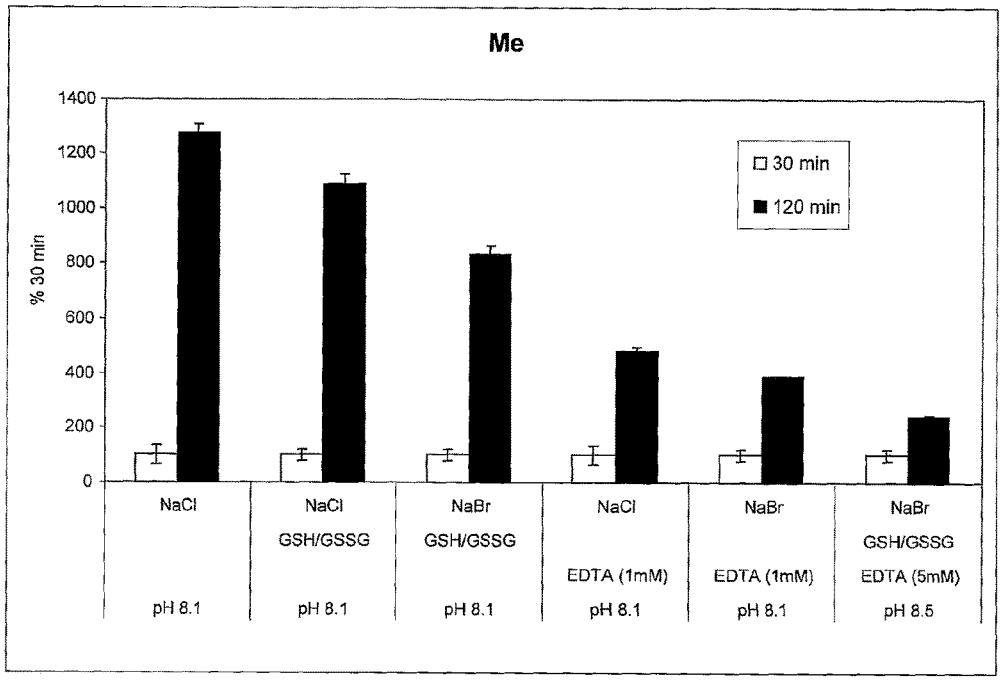
FIG. 26. shows the effect of combining NaCl or NaBr, chelating agent, detergent and oxidising agent on non-secreted Metridia luciferase activity.

HeLa cells expressing destabilised, non-secreted Metridia luciferase were plated in equal aliquots onto 96-well plates and incubated overnight. Medium was removed and the cells lysed in 20 ul of lysis buffer containing 5% glycerol, 63.4 uM sodium oxalate, 0.1% NP40, plus 25 mM Tris at the indicated pH, the indicated salt at 150 mM and, where indicated, 1 mM EDTA or 0.6 mM reduced glutathione and 0.4 mM oxidised glutathione (GSH/GSSG) Replicate samples were assayed for luciferase activity at 30 or 120 min after addition of lysis buffer by injecting 60 ul of assay buffer containing 25 mM Tris pH 7.75, 2 mM ascorbate, 24 uM Cz. Results were expressed as the % of the light units obtained at 30 min lysis (see FIG. 26).

The data show that with NaCl as the only additive, only a small portion of maximum activity is attained within the first 30 min of lysis. An increase of more than 1200% occurs between 30 and 120 min in this treatment group. Treatment groups comprising either a redox buffer (GSH/GSSG) or a chelator (EDTA) performed considerably better as indicated by the smaller increase in activity beyond 30 min lysis. In each case, NaBr performed better than NaCl demonstrating the additive benefit of combining bromide with redox buffer or chelator. The benefits of a combination of bromide, redox buffer, chelator and high pH can be clearly observed as the increase in activity between 30 and 120 min was less pronounced.

Collectively, these data demonstrate the cumulative benefit of combining multiple different components of the invention. Additionally, this data shows that the addition of bromide does not only improve signal strength (see Example 6 and FIGS. 5A and 5B), but also improves lysis time.

Part VII

Comparison to Prior Art

Example 28

HeLa cell expressing non-secreted Gaussia or Renilla luciferases were plated into 96-well plates and incubated overnight. Medium was removed and the cells lysed in 20 ul of GeneStream's v6 (as Example 26) lysis buffer or Promega's passive lysis buffer (PLB) per well. Luciferase activity was assayed by injecting 60 l of assay buffer comprising 25 mM Tris pH 7.75; 0.6 mM reduced glutathione, 0.4 mM oxidised glutathione, 1 mM EDTA, 2 mM Ascorbate, 24 uM Cz (see FIG. 27A). During the same experiment some wells were measured for luciferase activity without cell lysis by removing the medium and adding either 20 ul of fresh medium (RPMI) or phosphate buffered saline (PBS) and injecting 60 ul of assay buffer comprising 24 uM Cz in either RPMI or PBS onto the live cells (see FIG. 27B). Results are expressed as counts per second (CPS).

Figure 27A:
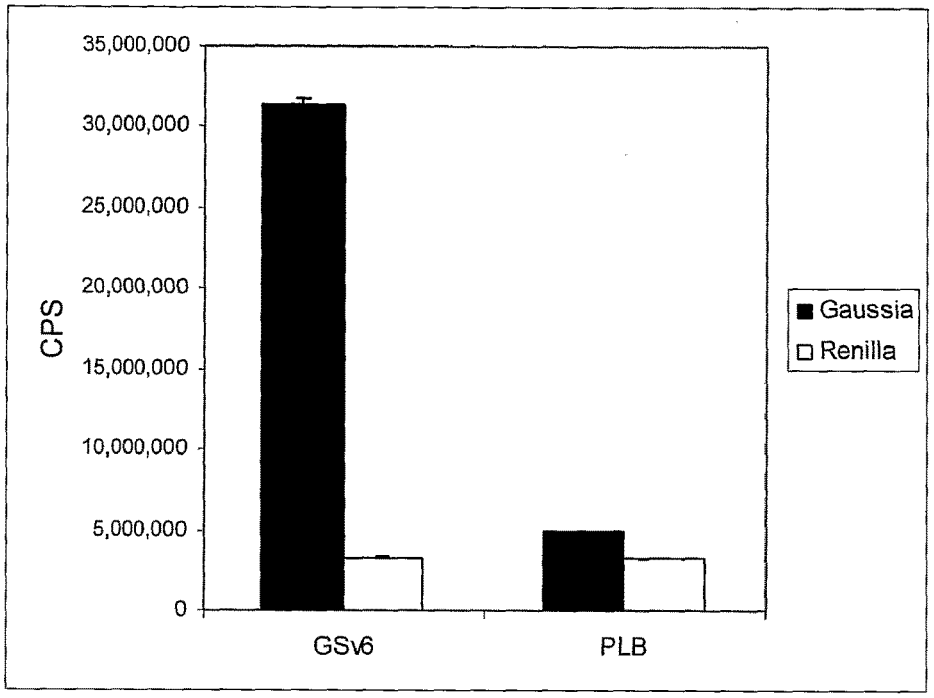
FIGS. 27A and 27B show a comparison of commercially available assay kits with a reagent composition according to an embodiment of the present invention with respect to on non-secreted Gaussia or Renilla luciferases.
Figure 27B:
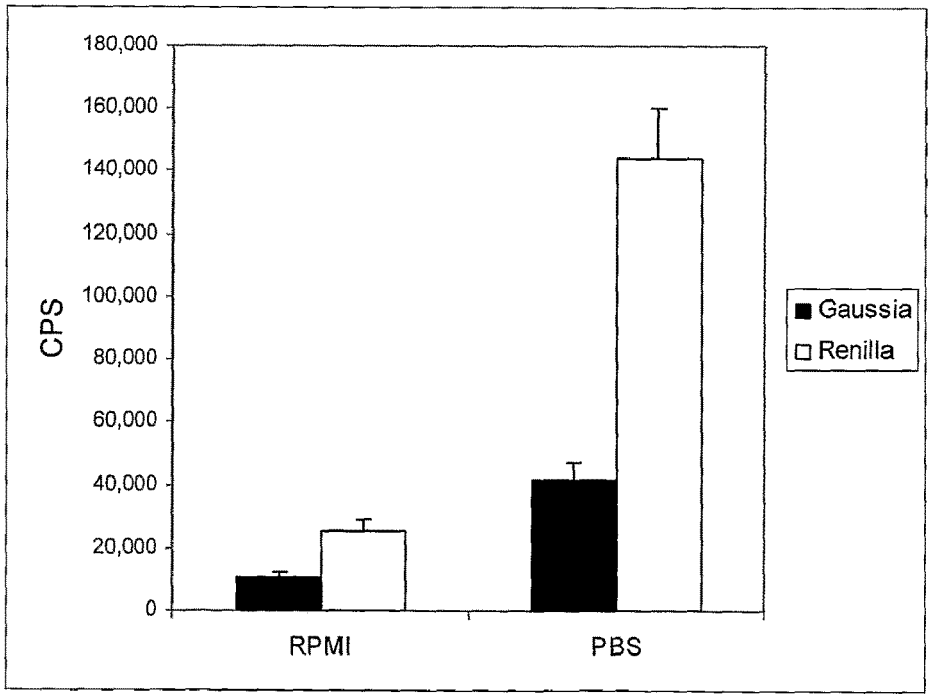

The results in FIG. 27A indicate that GeneStream's v6 (GSv6) buffer is at least as effect as Promega's passive lysis buffer (PLB) for use with Renilla luciferase but is superior (10-fold higher signal) to PLB for use with non-secreted Gaussia luciferase. The data shown in FIG. 27B shows that Renilla luciferase gives the strongest signal with live cells. The data combined indicates that Gaussia luciferase adopts a less active form at when expressed intracellularly.

Example 29

Figure 28:
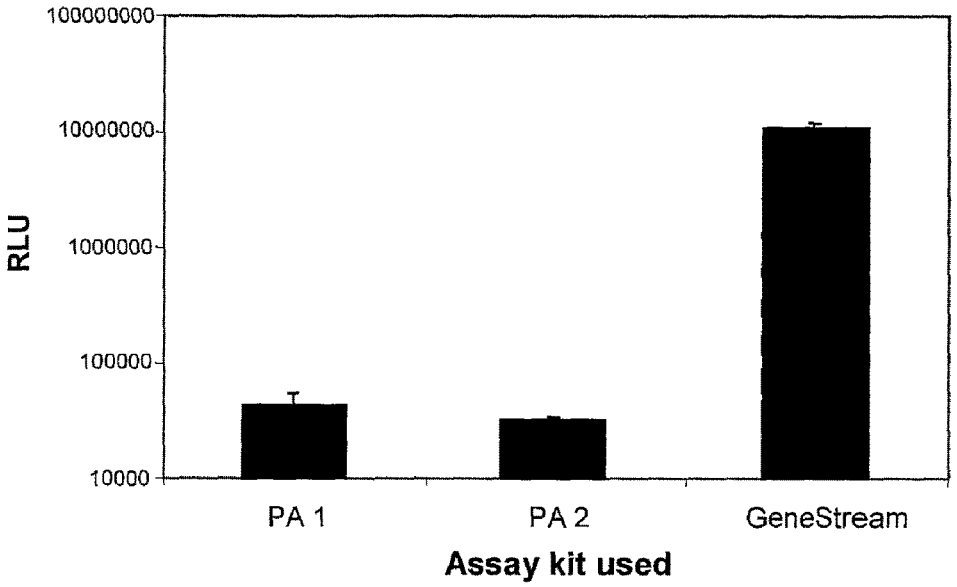
FIG. 28 shows a comparison of commercially available assay kits with a reagent composition according to an embodiment of the present invention with respect to sensitivity.

HeLa cells expressing destabilised, non-secreted Gaussia luciferase were plated in equal aliquots onto 96-well plates and incubated overnight (see FIG. 28). PA 1=luciferase assay performed with Promega's dual luciferase assay kit according to the manufacturer's instructions (i.e. cells lysed in passive lysis buffer and light emission measured after adding "Stop & Glo" (Renilla) assay buffer); PA 2=luciferase assay performed using Gaussia assay kit (NEB), cells lysed in passive lysis buffer (Promega) since the NEB assay kit does not include a lysis buffer; GeneStream=cells lysed and assayed according to the current invention (lysis buffer=0.1% NP40, 150 mM NaBr, 5% glycerol, 1 mM EDTA, pH 8.1; assay buffer=26 uM coelenterazine, 1 mM EDTA, pH 8.1.). Using compositions of the current invention, the signal intensity obtained was 252-fold higher than with PA 1 and 345-fold higher than with PA 2 (FIG. 28).

Example 30

Figure 29A:
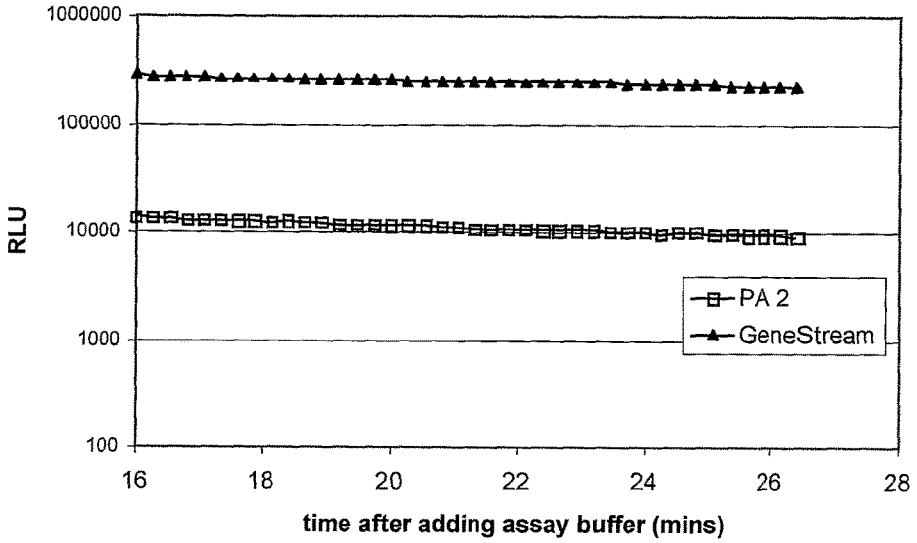
FIGS. 29A and 29B show a comparison of commercially available assay kits with a reagent composition according to an embodiment of the present invention with respect to prolonged glow.
Figure 29B:
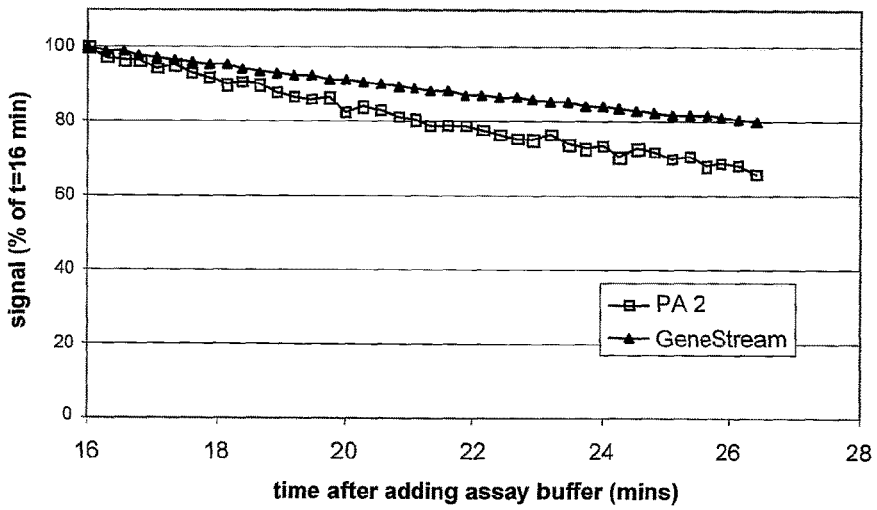

The method of Example 29 was followed except that the kinetics of light emission were measured. The data show that compared to a prior art "glow" buffer, the compositions that are the subject of the present invention provide a more stable glow signal and higher sensitivity (see FIGS. 29A and 29B).

Example 31

HeLa cells expressing destabilised, non-secreted Gaussia and non-secreted Metridia luciferase were plated in equal aliquots onto 96-well plates and incubated overnight. Medium was removed and the cells lysed in 20 ul of lysis buffer. Replicate samples were assayed for luciferase activity at 20, 30, 40, 60, 90 or 120 min after addition of lysis buffer. The lysis buffers used were GeneStream's v3 and v6 (as Example 26), Promega's passive lysis buffer (PLB) and a generic standard lysis buffer (STD-LB) containing 25 mM Tis pH 7.7; 1% Triton X100; 10% glycerol. Replicate samples were assayed for luciferase activity by injecting 60 ul of assay buffer containing 25 mM Tris pH 7.75; 1 mM EDTA, 2 mM ascorbate; 0.66 mM reduced glutathione, 0.4 mM oxidised glutathione, 24 uM Cz. Results were expressed as the % of the light units obtained using v6 lysis buffer (see FIG. 30A data at 120 min lysis) and % of the light units obtained with the same lysis buffer at 20 min (see FIG. 30B data at all lysis time points).

Figure 30A:
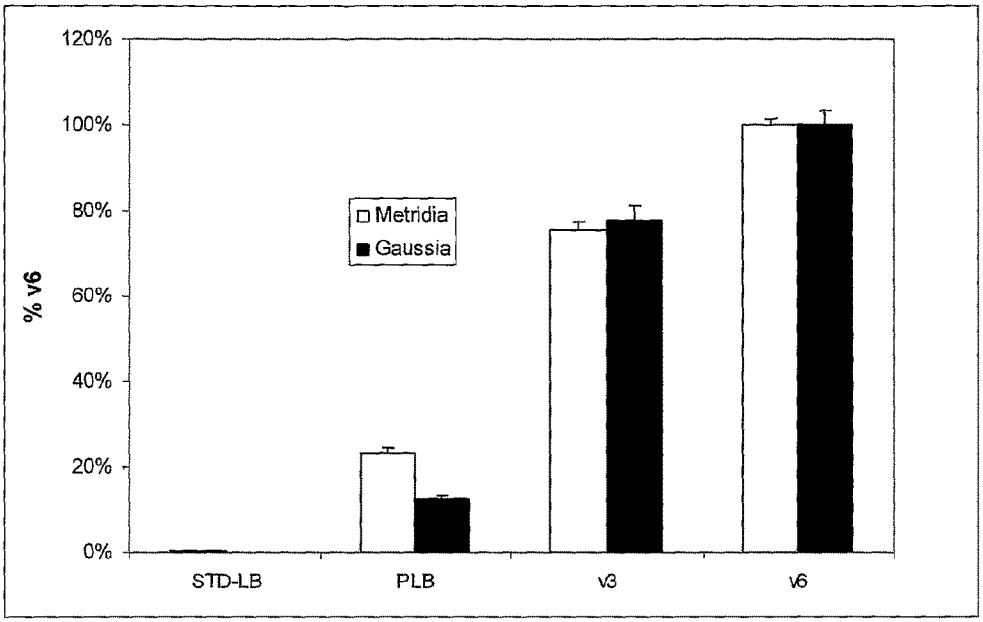
FIGS. 30A and 30B show a comparison of commercially available assay kits with a reagent composition according to an embodiment of the present invention with respect to sensitivity and effect of lysis time.
Figure 30B:
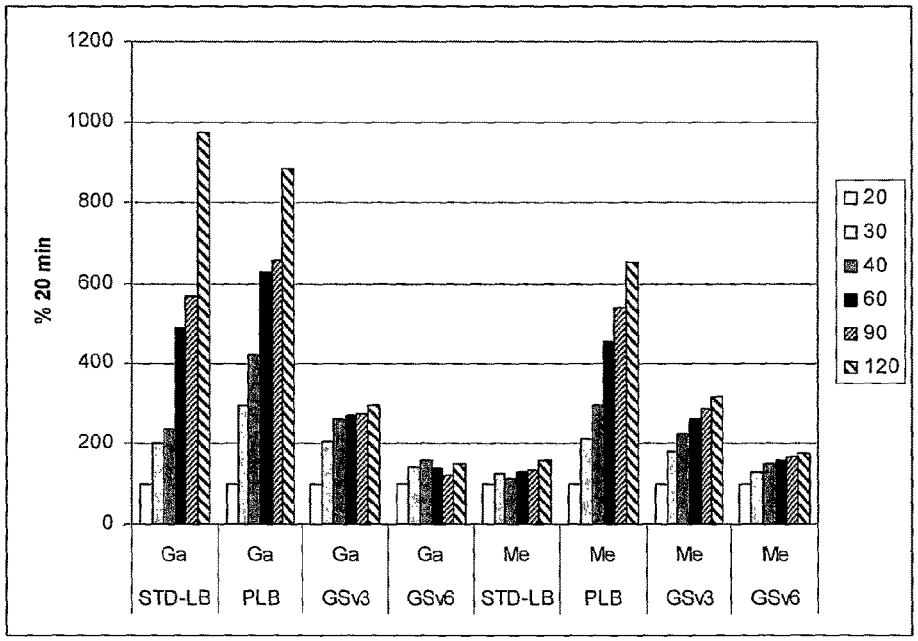

The data in FIG. 30A show that compared to prior art, the compositions that are the subject of the present invention provide a higher and more stable signal intensity for both non-secreted Gaussia luciferase and non-secreted Metridia luciferase. In addition, the data in FIG. 30B demonstrates that reduced lysis time can be employed when using the composition of the present invention compared to prior art compositions.

Part VIII

Luciferase-Based Gene Reporter Assay Kits According to the Invention

Example 32

Luciferase-based gene reporter assay kits according to the invention are provided in 2-parts designed for 20 ul lysis buffer and 60 ul assay buffer per well of a 96-well plate.

Lysis Buffer:
- 0.1% NP40
- 150 mM NaBr
- 5% glycerol
- 5 mM EDTA
- 25 mM Tris pH 8.5
- 63.4 uM sodium oxalate
- 0.6 mM reduced glutathione
- 0.4 mM oxidized glutathione Assay Buffer:
- 23.6 uM coelenterazine
- 1 mM EDTA
- 25 mM Tris pH 7.75
- 0.6 mM reduced glutathione
- 0.4 mM oxidised glutathione
- 2 mM ascorbate
- 75 mM urea General Method:

HeLa cells expressing a modified non-secreted Gaussia luciferase are cultured in 96-well plates, lysed with lysis buffer (20 ul) after removing any medium and are assayed for luciferase activity using a Wallac Victor 3 luminometer (Perkin Elmer) in flash reactions following injection of assay buffer (60 ul).

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification individually or collectively, and any and all combinations of any two or more of said steps or features.

The invention claimed is:

[1. A method for conducting a luciferase-based assay comprising, expressing within a eukaryotic cell a luciferase that is secreted in its native form, wherein the luciferase lacks a functional signal peptide such that it is expressed intracellularly in the eukaryotic cell;

recovering the activity of the luciferase by contacting the luciferase with a reagent composition that provides an environment suitable for conversion of the luciferase into its active folded form, wherein the reagent composition comprises an agent selected from the group consisting of bromide anion, chelator, redox buffer, and buffer with a pH greater than 8.0;

contacting the luciferase with a substrate of the luciferase enzyme; and detecting or measuring the bioluminescence.]

[2. The method of claim 1, wherein the luciferase in its active form includes disulphide bonds between cysteine residues.]

[3. The method of claim 1, wherein the recovering activity comprises a cell lysis step.]

[4. The method of claim 1, wherein the method is employed in a reporter gene assay.]

[5. A method for conducting a luciferase-based assay comprising, expressing within a eukaryotic cell a luciferase that is secreted in its native form, wherein the luciferase lacks a functional signal peptide such that it is expressed intracellularly in the eukaryotic cell;

recovering the activity of the luciferase by contacting the luciferase with a reagent composition that provides an environment suitable for conversion of the luciferase into its active folded form, wherein the reagent composition comprises an oxidising agent;

contacting the luciferase with a substrate of the luciferase enzyme; and detecting or measuring the bioluminescence.]

[6. The method of claim 5, wherein the luciferase in its active form includes disulphide bonds between cysteine residues.]

[7. The method of claim 5, wherein the recovering activity comprises a cell lysis step.]

[8. The method of claim 5, wherein the method is employed in a reporter gene assay.]

*9. A method for determining the amount and/or activity of a recombinant luciferase in a cell or sample of cells, the method comprising:*

*a) contacting the cell or sample of cells with a reagent composition comprising a detergent and one or more of bromide anion, a chelator, an oxidizing agent, redox buffer, and a buffer with a pH greater than 8.0;*

*b) adding a substrate of the luciferase; and*

*c) detecting bioluminescence in the sample;*

*wherein the recombinant luciferase is a non-secreted variant or derivative of a luciferase that is secreted in its native form.*

*10. The method of claim 9, wherein step (b) occurs simultaneously with, or following step (a).*

*11. The method of claim 9, wherein the luciferase lacks a functional signal peptide.*

*12. The method of claim 9, wherein the detergent is a non-ionic or zwitterionic detergent.*

*13. A method for determining the amount and/or activity of a recombinant luciferase in a cell or sample of cells, the method comprising:*

*a) contacting the cell or sample of cells with a reagent composition that lyses the cell or sample of cells and provides an environment that enables conversion of the luciferase into an active state, comprising a detergent and one or more of bromide anion, a chelator, an oxidizing agent, redox buffer, and a buffer with a pH greater than 8.0;*

*b) adding a substrate of the luciferase; and*

*c) detecting bioluminescence in the sample;*

*wherein the recombinant luciferase is a non-secreted variant or derivative of a luciferase that is secreted in its native form.*

*14. The method of claim 13, wherein conversion of the luciferase into an active state means either the conversion from an inactive state to an active state, or the conversion from a partially active or less active state to a more active state.*

*15. The method of claim 13, wherein the detergent is a non-ionic or zwitterionic detergent.*

*16. A method for increasing the bioluminescent signal generated by a recombinant luciferase, the method comprising:*

*a) contacting the recombinant luciferase with a reagent composition comprising one or more of bromide anion, a chelator, an oxidizing agent, redox buffer, and a buffer with a pH greater than 8.0;*

*b) adding a substrate of the luciferase; and*

*c) detecting bioluminescence in the sample;*

*wherein the recombinant luciferase is a non-secreted variant or derivative of a luciferase that is secreted in its native form.*

*17. The method of claim 16, wherein step (b) occurs simultaneously with, or following step (a).*

*18. The method of claim 16, wherein the luciferase lacks a functional signal peptide.*

*19. The method of claim 16, wherein the reagent composition further comprises a detergent selected from a non-ionic or zwitterionic detergent.*

*20. A method for increasing the bioluminescent signal generated by a recombinant luciferase, the method comprising:*

*a) contacting the recombinant luciferase with a reagent composition that provides an environment that enables conversion of the luciferase into an active state, comprising one or more of bromide anion, a chelator, an oxidizing agent, redox buffer, and a buffer with a pH greater than 8.0;*

*b) adding a substrate of the luciferase; and*

*c) detecting bioluminescence in the sample;*

*wherein the recombinant luciferase is a non-secreted variant or derivative of a luciferase that is secreted in its native form.*

*21. The method of claim 20, wherein conversion of the luciferase into an active state means either the conversion from an inactive state to an active state, or the conversion from a partially active or less active state to a more active state.*

*22. A method for reducing the rate of decay of the bioluminescent signal generated by a recombinant luciferase, the method comprising:*

*a) contacting the recombinant luciferase with a reagent composition comprising one or more of bromide anion, a chelator, an oxidizing agent, redox buffer, and a buffer with a pH greater than 8.0;*

*b) adding a substrate of the luciferase; and*

*c) detecting bioluminescence in the sample;*

*wherein the recombinant luciferase is a non-secreted variant or derivative of a luciferase that is secreted in its native form.*

*23. The method of claim 22, wherein step (b) occurs simultaneously with, or following step (a).*

*24. The method of claim 22, wherein the luciferase lacks a functional signal peptide.*

*25. The method of claim 22, wherein the reagent composition further comprises a detergent selected from a non-ionic or zwitterionic detergent.*

*26. A method for reducing the rate of decay of the bioluminescent signal generated by a recombinant luciferase, the method comprising:*

*a) contacting the recombinant luciferase with a reagent composition that provides an environment that enables conversion of the luciferase into an active state, comprising one or more of bromide anion, a chelator, an oxidizing agent, redox buffer, and a buffer with a pH greater than 8.0;*

*b) adding a substrate of the luciferase; and*

*c) detecting bioluminescence in the sample;*

*wherein the recombinant luciferase is a non-secreted variant or derivative of a luciferase that is secreted in its native form.*

*27. The method of claim 26, wherein conversion of the luciferase into an active state means either the conversion from an inactive state to an active state, or the conversion from a partially active or less active state to a more active state.*

* * * * *